United States Patent
Charych et al.

(10) Patent No.: US 6,485,987 B1
(45) Date of Patent: Nov. 26, 2002

(54) SOL-GEL MATRICES FOR DIRECT COLORIMETRIC DETECTION OF ANALYTES

(75) Inventors: Deborah H. Charych, Albany, CA (US); Darryl Sasaki, Albuquerque, NM (US); Stacey Yamanaka, Dallas, TX (US)

(73) Assignees: Regents of the University of California, Oakland, CA (US); Sandia Corporation, NM (US)

(*) Notice: Subject to any disclaimer, the term of this patent is extended or adjusted under 35 U.S.C. 154(b) by 0 days.

(21) Appl. No.: 09/500,295

(22) Filed: Feb. 8, 2000

Related U.S. Application Data

(62) Division of application No. 08/920,501, filed on Aug. 29, 1997, now Pat. No. 6,022,748.

(51) Int. Cl.$^7$ .................... G01N 33/552; G01N 33/549
(52) U.S. Cl. .................. 436/535; 435/7.2; 435/7.4; 435/7.32; 435/188; 436/527; 436/528; 436/531; 436/805; 436/811; 436/815; 436/823; 436/829
(58) Field of Search ................. 424/1.21, 450; 435/188, 7.32, 7.4, 7.2; 436/527, 528, 535, 805, 811, 815, 823, 829, 531

(56) References Cited

U.S. PATENT DOCUMENTS

| | | |
|---|---|---|
| 4,859,538 A | 8/1989 | Ribi |
| 5,200,334 A | 4/1993 | Dunn et al. |
| 5,268,305 A | 12/1993 | Ribi et al. |
| 5,300,564 A * | 4/1994 | Avnir et al. ............... 525/54.1 |
| 5,415,999 A | 5/1995 | Saul et al. |
| 5,427,915 A | 6/1995 | Ribi et al. |
| 5,480,582 A | 1/1996 | Pope |
| 5,491,097 A | 2/1996 | Ribi et al. |
| 5,521,101 A | 5/1996 | Saini et al. |
| 5,571,568 A | 11/1996 | Ribi et al. |
| 5,591,453 A | 1/1997 | Ducheyne et al. |
| 5,618,735 A | 4/1997 | Saul et al. |
| 5,622,872 A | 4/1997 | Ribi |
| 5,637,507 A | 6/1997 | Wicks et al. |

OTHER PUBLICATIONS

Adlish et al., "Identification of a Putative Cell Receptor for Human Cytomegalovirus," *Virology* 176:337–345 [1990].
Avnir, "Organic Chemistry within Ceramic Matrices: Doped Sol–Gel Materials," *Acc. Chem. Res.* 28: 328–334 [1995].
Beswick and Pitt, "Optical Detection of Toxic Gases Using Fluorescent Porphyrin Langmuir–Blodgett Films," *J. Colloid Interface Sci.* 124: 146–155 [1988].
Bilewicz and Majda, "Monomolecular Langmuir–Blodgett Films at Electrodes. Formation of Passivating Monolayers and Incorporation of Electroactive Reagents," *Langmuir* 7: 2794–2802 [1991].
Binnig et al., "Atomic Force Microscope," *Phys. Rev. Lett.* 12: 930–933 [1986].
Binnig et al., "Atomic Resolution with Atomic Force Microscope," *Europhys. Lett.* 3: 1281–1286 [1987].
Carel et al., "Structural Requirements for C3d, g/Epsten–Barr Virus Receptor (CR2/CD21) Ligand Binding, Internalization, and Viral Infection," *J. Biol. Chem.* 265: 12293–12299 [1990].
Carey, "Multivariate sensor arrays as industrial and environmental monitoring systems," *Trends Anal. Chem.* 13: 210–218 [1993].
Carey and Kowalski, "Monitoring a Dryer Operation Using an Array of Piezoelectric Crystals," *Anal. Chem.* 60: 541–544 [1988].
Charych et al., "Direct Colorimetric Detection of a Receptor–Ligand Interaction by a Polymerized Bilayer Assembly," *Science* 261:585–588 (1993).
Co et al., "Isolation and biochemical characterization of the mamalian reovirus type 3 cell–surface receptor," *Proc. Natl. Acad. Sci.* 82: 1494–1498 [1995].
Dave et al., "Sol–gel Encapsulation Methods for Biosensors," *Anal. Chem.* 66: 1120A–1127A [1994].
Day and Lando, "Morphology of Crystalline Diacetylene Monolayers Polymerized at the Gas–Water Interface," *Macromolecules* 13: 1478–1483 [1980].
Eppstein et al., "Epidermal growth factor receptor occupancy inhibits vaccinia virus infection," *Nature* 318: 663–665 [1985].
Finegold and Martin, *Diagnostic Microbiology*, 6th Ed. (1982), CV Mosby St. Louis, pp 13–15.
Furuki and Pu, "Hybrid gas detector of squarylium dye Langmuir–Blodgett film deposited on a quartz oscillator," *Thin Solid Films* 210: 471–473 [1992].
Gronow, "Biosensors," *Trends Biochem. Sci* 9: 336–340 [1984].
Kaner et al., "Fibroblast Growth Factor Receptor Is a Portal of Cellular Entry for Herpes Simplex Virus Type 1," *Science* 248: 1410–1413 [1990].
Karpe et al., "Thermal–desorption–gas chromatography–mass spectrometry–flame ionization detection–sniffer multi–coupling: A device for the determination of odorous volatile organic compounds in air," *J. Chromatography* A 708: 105–114 [1995].
Kepley et al., "Selective Surface Acoustic Wave–Based Organophosphonate Chemical Sensor Employing a Self–Assembled Composite Monolayer: A New Paradigm for Sensor Design," *Anal. Chem.* 64: 3191–3193 [1992].

(List continued on next page.)

*Primary Examiner*—Mary E. Ceperley
(74) *Attorney, Agent, or Firm*—Medlen & Carroll, LLP

(57) ABSTRACT

The present invention relates to methods and compositions for the direct detection of analytes using color changes that occur in immobilized biopolymeric material in response to selective binding of analytes to their surface. In particular, the present invention provides methods and compositions related to the encapsulation of biopolymeric material into metal oxide glass using the sol-gel method.

23 Claims, 16 Drawing Sheets

OTHER PUBLICATIONS

Kolbe et al., "Atomic force microscopy imaging of T4 bacteriophages on silicon substrates," *Ultramicroscopy* 42–44: 1113–1117 [1992].

Krah et al., "Characterization of Octyl Glucoside–Solubilized Cell Membrane Receptors for Binding Measles Virus," *Virology* 172: 386–390 [1989].

Krämer, "Biosensors for Measuring Pesticide Residues in the Environment Past, Present, and Future," *J. AOAC Intern.* 79:1245–1254 [1996].

Lentz et al., "Is the Acetylcholine Receptor a Rabies Virus Receptor," *Science* 215: 182–184 [1982].

Marlin et al., "A soluble form of intercelluar adhesion molecule–1 inhibits rhinovirus infection," *Nature* 344: 70–72 [1990].

Mendelsohn et al., "Cellular Receptor for Poliovirus: Molecular Cloning, Nucleotide Sequence, and Expression of a New Member of the Immunoglobin Superfamily," *Cell* 56: 855–865 –865 [1989].

Miller et al., "Synthesis conditions for encapsulating cytochrome *c* and catalase in $SiO_2$ sol–gel materials," *J. Non-–Cryst. Solids* 202: 279–289 [1996].

Miyasaka et al., "Amperometric Glucose Sensor with Glucose Oxidase Immobilized on SnO2 Electrode via a Monolayer of a Photoreactive Nitrophenylazide Derivative," *Chem. Lett.*,pp. 627–630 (1990).

New, *Liposomes : A Pratical Approach*, Oxford University Press, Oxford, pp 33–104 [1990].

Okahata and Kunitake, "Formation of Stable Monolayer Membranes and Related Structurs in Dilute Aqueous Solution from Two–Headed *Ammonium Amphiphiles,*" *J. Am. Chem. Soc.*101: 5231–5234 [1979].

Pan and Charych, "Molecular Recognition and Colorimetric Detection of Cholera Toxin by Poly(diacetylene) Liposomes Incorporating G hd M1 Ganglioside," *Langmuir* 13:1365–1367 [1997].

Paulson, "Interactions of Animal Viruses with Cell Surface Receptors," in *The Receptors* , Conn (ed.), Academic Press, New York, vol. 2, pp 131–219 [1985].

Reichert et al., "Polydiacetylene Liposomes Functionalized with Sialic Acid Bind and Colorimetrically Detect Influenza Virus," *J. Am. Chem. Soc.* 117:829–830 [1995].

Rose–Phersson et al., "Detection of Hazardous Vapors Including Mixtures Using Recognition Analysis of Responses from Surface Acoustic Wave Devices," *Anal. Chem.* 60: 2801–2811 [1999].

Ruff et al., "CD4 receptor binding peptides that block HIV infectivity cause human monocyte chemotaxis," *FEBS Lett.* 211: 17–22 [1987].

Sacerdote et al., "Vasoactive Intestinal Peptide 1–12: A Ligand for the CD4 (T4)/Human Immunodeficiency Virus Receptor," *J. Neuroscience Res.* 18: 102–107 [1987].

Shepley et al., "Monoclonal antibody identification of a 100–kDa membrane protein in HeLa cells and human spinal cord involved in polovirus attachment,"0 *Proc. Natl. Acad. Sci* .85: 7743–7747 [1988].

Spevak et al., "Polymerized Liposomes Containing C–Glycosides of Sialic Acid: Potent Inhibitors Virus in Vitro Infectivity," *J. Am. Chem. Soc.* 115: 1146–1147 [1993].

Weis et al., "Structure of the influenza virus haemagglutinin complexed with its receptor, sialic acid," *Nature* 333: 426–431 [1988].

White et al., "Viral Receptors of the Immunoglobulin Superfamily," *Cell* 56:725–728 [1989].

Wyrick et al. "Entry of Genital *Chlamydia trachomatis* into Polarized Human Epithelial Cells," *Infect. Immun.* 57: 2378–2389 [1989].

Yamanaka et al., "Nicotinamide Adenine Dinucleotide Phosphate Fluorescence and Absorption Monitoring of Enzymatic Activity in Silicate Sol–Gels for Chemical Sensing Applications," *J. Am. Chem . Soc.* 117: 9095–9096 [1995].

Zhao and Reichert, "Influence of Biotin Lipid Surface Density and Accessibility on Avidin Binding to the Tip of an Optical Fiber Sensor," *Langmuir* 8: 2785–2791 [1992].

Ellerby et al., "Encapsulation of Proteins in Transparent Porous Silicate Glasses Prepared by the Sol–Gel Method," *Science* 225:1113–1115 (1992) .

Charych et al., "Specific Interaction of Influenza Virus with Organized Assemblies of Polydiacetylenes," *Mat. Res. Soc. Symp. Proc.* 282:153–161 (1993).

Spevak, "The Presentation of Biological Ligands on the Surface of Polymerized Monolayers and Liposomes," Ph.D. Dissertation, University of California at Berkeley (1993).

Pons et al., "The Optical Activity and Circular Dichroic Spectra of Diacetylenic Phospholipid Polymers," *Biochim. Biophys. Acta* 693:461–465 (1982).

Kaneko et al., "Absorption properties and structure changes caused by pre–annealing in polydiacetylene Langmuir–Blodgett Films," *Thin Solid Films* 210/211:548–550 (1989).

Shibata et al., "Reversible Colour Phase Transitions and Annealing Properties of Langmuir–Blodgett Polydiacetylene Films," *Thin Solid Films* 179:433–437 (1989).

Lio et al., "Atomic force microscope study of chromatic transitions in polydiacetylene thin films," *J. Vac. Sci. Technol.* 14(2):1481–1486 (1996).

Leung et al., "Imaging of polydiacetylene on graphite by scanning tunneling microscopy," *J. Appl. Phys.* 69(4):2044–2047 (1991).

Rieke et al., "Spatially Resolved Mineral Deposition on Patterned Self–Assembly Monolayers," *Langmuir* 10:619–622 (1994).

Dagani, "Lipids and Minerals Form Novel Composite Microstructures," *Chem. & Eng. News*, 19–20 (1993).

Yamanaka et al., "Solid Phase Immobolization of Optically Responsive Liposomes in Sol–gel Materials for Chemical and Biological Sensing," *Langmuir* 13:5049–5053 (1997).

* cited by examiner

FIGURE 9B

| Solvent | Saturation concentration in water (wt%) | Solvent | Saturation concentration in water (wt%) |
|---|---|---|---|
| hexane | 0.0011 | 1-octanol | 0.054 |
| cyclohexane | 0.0055 | 1-hexane | 0.077 |
| diethylether | 6.0 | 1-butanol | 7.45 |
| toluene | 0.051 | $CCl_4$ | 0.077 |
| benzene | 0.179 | $CHCl_3$ | 0.815 |
| | | $CH2Cl_2$ | 1.3 |

FIGURE 12A
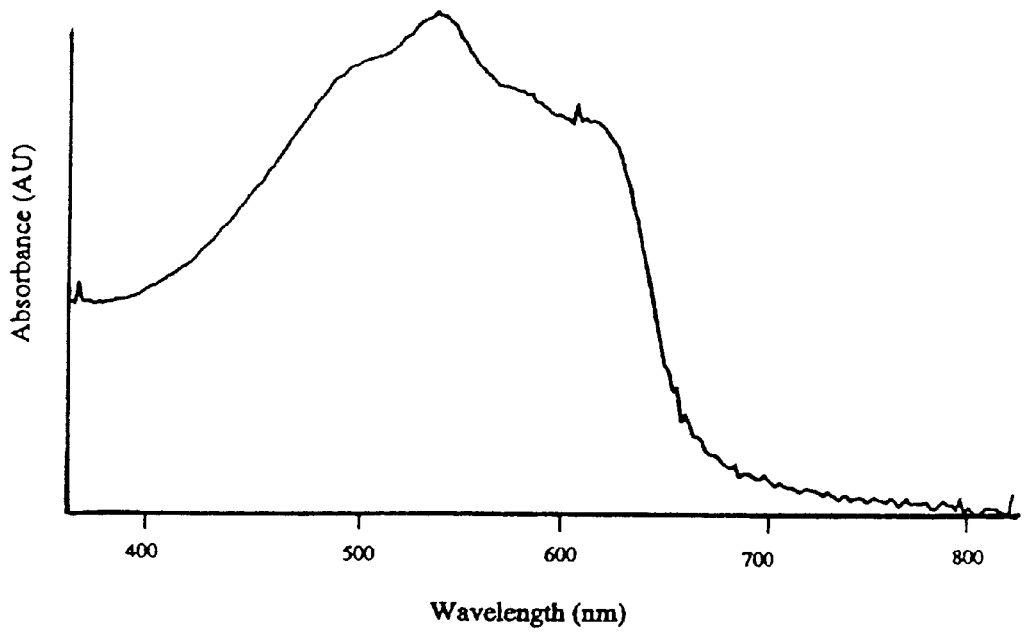
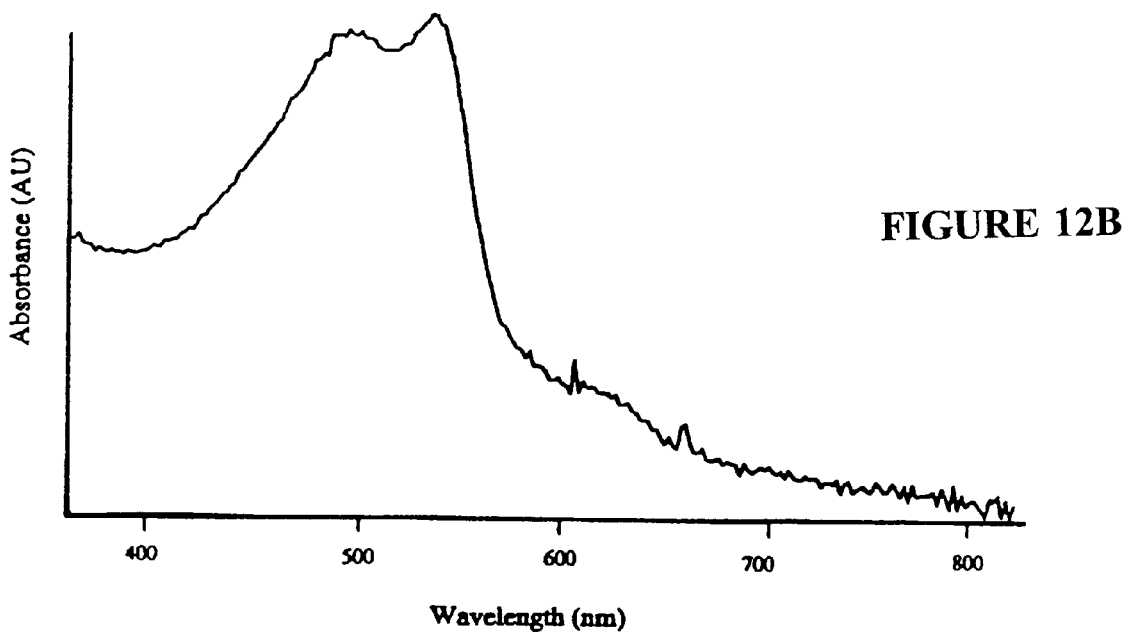
FIGURE 12B

ACIDIC HEAD GROUP 2.4 (PDA)

2.5 (GLY-PDA)

NEUTRAL HEAD GROUP 2.6 (EA-PDA)

2.7

BASIC HEAD GROUP 2.8 (EDA-PDA)

2.9 (PEG-PDA)

ZWITTERIONIC HEAD GROUP 2.10

HYDROPHOBIC HEAD GROUP 2.11

2.12

2.13

SOL-GEL MATRICES FOR DIRECT COLORIMETRIC DETECTION OF ANALYTES

This is a divisional of application Ser. No. 08/920,501, filed Aug. 29,1997, now U.S. Pat. No. 6,022,748.

FIELD OF THE INVENTION

The present invention relates to methods and compositions for the direct detection of analytes using color changes that occur in immobilized biopolymeric material in response to selective binding of analytes to their surface.

BACKGROUND OF THE INVENTION

A major goal of analyte detection research is to develop inexpensive, fast, reliable, and sensitive detectors. Unfortunately, the technologies developed to date have only met some of these goals, and no single device has sufficiently attained a majority of them.

Classical detection methods such as liquid chromatography (LC), gas chromatography (GC), and supercritical fluid chromatography (SFC), in combination with mass spectrometry, are widely used and provide accurate identification of analytes and quantitative data. However, these techniques are time consuming, extremely expensive, require sample preconcentration, and are difficult or impossible to adapt to field use.

Biosensors (i.e., devices containing biological material linked to a transducing apparatus) have been developed to overcome some of the shortcomings of the classical analyte detection techniques. Many currently used biosensors are associated with transducer devices that use photometry, fluorimetry, and chemiluminescence; fiber optics and direct optical sensing (e.g., grating coupler); surface plasmon resonance; potendiometric and amperometric electrodes; field effect transistors; piezoelectric sensing; and surface acoustic wave (Krämer, J. AOAC Intern. 79: 1245 [1996]). However, there are major drawbacks to these devices, including their dependence on a transducing device, which prevents miniaturization and requires a power source. These disadvantages make such devices too complex, expensive, or unmanageable for many routine analyte detection applications such as field work or home use. Additionally, many of these devices are limited by the lack of stability and availability of the biological materials (e.g., proteins, antibodies, cells, and organelles).

Immunoassay methods are also used for detecting certain types of analytes. In these methods, antibodies are developed to specifically bind to a target of interest (e.g., an analyte). By labeling the antibody (e.g., with dye or fluorescent or radioactive material), binding of the antibody to an analyte can be detected. However, immunoassay methods are limited in that they require production of antibodies against each analyte of interest. Antibodies cannot be generated against some types of analytes and their generation can be time consuming and expensive.

The art remains in need of analyte detectors that provide the specificity of biosensors but also provide the cost-efficiency, stability, accuracy, reliability, reproducibility, and robustness that is lacking from available technologies. In particular, development of devices that can be miniaturized with controlled shapes and that do not rely on an energy source would also be very beneficial, particularly for routine field work and home use.

SUMMARY OF THE INVENTION

The present invention relates to methods and compositions for the direct detection of analytes using color changes that occur in immobilized biopolymeric material in response to selective binding of analytes to their surface.

The present invention provides various methods and compositions useful for the detection of analytes.

In one embodiment, the present invention provides methods for immobilizing biopolymeric material: providing a metal oxide, biopolymeric material, an acid, a buffer, and a sonicating means; sonicating the metal oxide and the acid using the sonicating means to produce a sonicated solution; adding the buffer to the sonicated solution to produce a buffered solution; and adding the biopolymeric material to the buffered solution to produce an organic/inorganic solution.

In alternative embodiments of the methods, the present invention further comprises the steps of applying the organic/inorganic solution to a formation support to produce a formed organic/inorganic solution; and gelling the formed organic/inorganic solution to produce an organic/inorganic device.

In preferred embodiments, the metal oxide comprises tetramethylorthosilicate, although it is contemplated that any material that can be used to produce substantially transparent, porous glass will be used in the methods of the present invention.

In some embodiments, the biopolymeric material is selected from the group consisting of liposomes, films, multilayers, braided, lamellar, helical, tubular, and fiber-like shapes, solvated rods, solvated coils, and combinations thereof.

In other embodiments, the biopolymeric material comprises a plurality of self-assembling monomers selected from the group consisting of diacetylenes, acetylenes, alkenes, thiophenes, polythiophenes, imides, acrylamides, methacrylates, vinylether, malic anhydride, urethanes, allylamines, siloxanes anilines, pyrroles, vinylpyridinium, and combinations thereof, although any self-assembling monomer that will form biopolymeric material is contemplated by the present invention. In preferred embodiments, the diacetylenes are selected from a group consisting of 5,7-docosadiynoic acid, 10,12-pentacosadiynoic acid, 5,7-pentacosadiynoic acid, and combinations thereof. In yet other embodiments, the self-assembling monomers contain head groups selected from the group consisting of carboxylic acid, hydroxyl groups, amine groups, amino acid derivatives, and hydrophobic groups, although any head group that exists or can be synthesized on self-assembling monomers is contemplated by the presently claimed invention.

In some preferred embodiments, the biopolymeric material further comprises a ligand. In some embodiments, the ligand is selected from the group consisting of peptides, carbohydrates, nucleic acids, biotin, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, antibodies, and combinations thereof, although any ligand that can be linked to, or associated with, biopolymeric material is contemplated by the present invention.

In some preferred embodiments, the acid comprises hydrochloric acid, while in other preferred embodiments, the buffer comprises 3-[N-Morpholino]propanesulfonic acid. In other embodiments, the sonicating is conducted at a temperature from 0° C. to 20° C.

The present invention further provides an organic/inoiganic device produced according to any and all of the methods described above. In addition, the present invention provides biopolymeric material encapsulated in sol-gel glass. In some embodiments, the glass comprises tetramethylorthosilicate.

In some preferred embodiments, the biopolymeric material encapsulated in sol-gel glass is selected from the group consisting of liposomes, films, multilayers, braided, lamellar, helical, tubular, and fiber-like shapes, solvated rods, solvated coils, and combinations thereof. In particularly preferred embodiments, the biopolymeric material comprises self-assembling monomer selected from the group consisting of diacetylenes, acetylenes, alkenes, thiophenes, polythiophenes, imides, acrylamides, methacrylates, vinylether, malic anhydride, urethanes, allylamines, siloxanes anilines, pyrroles, vinylpyridinium, and combinations thereof, although any self-assembling monomer that will form biopolymeric material is contemplated by the present invention. In preferred embodiments, the diacetylenes are selected from a group consisting of 5,7-docosadiynoic acid, 10,12-pentacosadiynoic acid, 5,7-pentacosadiynoic acid, and combinations thereof. In yet other embodiments, the self-assembling monomers contain head groups selected from the group consisting of carboxylic acid, hydroxyl groups, amine groups, amino acid derivatives, and hydrophobic groups, although any head group that exists or can be synthesized on self-assembling monomers is contemplated by the presently claimed invention.

In some preferred embodiments, the biopolymeric material encapsulated in sol-gel glass further comprises a ligand. In some embodiments, the ligand is selected from the group consisting of peptides, carbohydrates, nucleic acids, biotin, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, antibodies, and combinations thereof, although any ligand that can be linked to, or associated with, biopolymeric material is contemplated by the present invention.

The present invention further provides methods for detecting analytes: providing biopolymeric material encapsulated in sol-gel glass, a detection means, and one or more analyte; exposing the biopolymeric material encapsulated in sol-gel glass to the analyte to produce a response; and detecting said response using the detection means.

In preferred embodiments, the glass comprises tetramethylorthosilicate, although it is contemplated that any material that can be used to produce substantially transparent, porous glass will be used in the methods of the present invention.

In some embodiments, the biopolymeric material is selected from the group consisting of liposomes, films, multilayers, braided, lamellar, helical, tubular, and fiber-like shapes, solvated rods, solvated coils, and combinations thereof.

In other embodiments, the biopolymeric material comprises a plurality of self-assembling monomers selected from the group consisting of diacetylenes, acetylenes, alkenes, thiophenes, polythiophenes, imides, acrylamides, methacrylates, vinylether, malic anhydride, urethanes, allylamines, siloxanes anilines, pyrroles, vinylpyridinium, and combinations thereof, although any self-assembling monomer that will form biopolymeric material is contemplated by the present invention. In preferred embodiments, the diacetylenes are selected from a group consisting of 5,7-docosadiynoic acid, 10,12-pentacosadiynoic acid, 5,7-pentacosadiynoic acid, and combinations thereof. In yet other embodiments, the self-assembling monomers contain head groups selected from the group consisting of carboxylic acid, hydroxyl groups, amine groups, amino acid derivatives, and hydrophobic groups, although any head group that exists or can be synthesized on self-assembling monomers is contemplated by the presently claimed invention.

In some preferred embodiments, the biopolymeric material further comprises a ligand. In some embodiments, the ligand is selected from the group consisting of peptides, carbohydrates, nucleic acids, biotin, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, antibodies, and combinations thereof, although any ligand that can be linked to, or associated with, biopolymeric material is contemplated by the present invention.

In some embodiments, the analyte is selected from the group consisting of small molecules, pathogens, bacteria, membrane receptors, membrane fragments, enzymes, drugs, antibodies, and combinations thereof, although any analyte that can be detected through its interaction with a ligand or the biopolymeric material is contemplated by the present invention.

In yet other embodiments, the biopolymeric material encapsulated in sol-gel glass comprises a badge.

In preferred embodiments, the detection means is selected from the group consisting of visual inspection, spectrometry, optical fiber, quartz oscillators, electrode surfaces, and scintillation, although any detection means that provides analysis of the presence of an analyte is contemplated by the present invention.

In some embodiments, the response is used as a competitive binding measurement to quantitate and characterize the presence of natural binding sites. In other embodiments, the biopolymeric material encapsulated in sol-gel glass comprises an array.

DESCRIPTION OF THE FIGURES

FIG. 12 shows a visible absorption spectrum of sialic acid-linked PDA; A) before; and B) after exposure to cholera toxin.

GENERAL DESCRIPTION OF THE INVENTION

Figure 1:
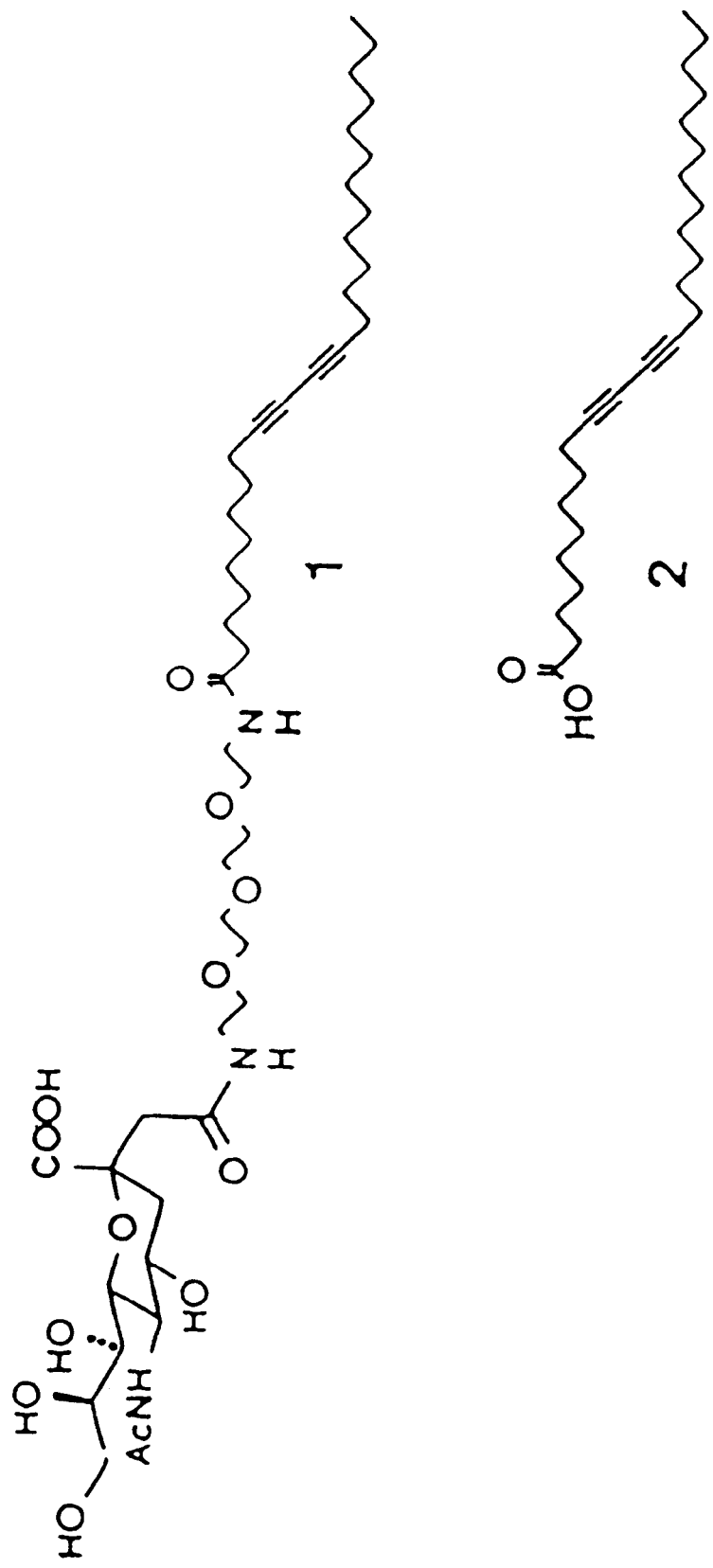
FIG. 1 shows a diagram of a receptor-linker-ligand complex where compound 1 shows a sialic acid group attached to 10,12-pentacosadiynoic acid (compound 2) through a linker group.

The present invention relates to methods and compositions for the direct detection of analytes using color changes in immobilized biopolymeric material that occur in response to selective binding of analytes to their surface. In particular, the present invention provides methods and compositions related to polymerized biological materials immobilized in porous glass that undergo conformational changes when exposed to analytes, producing a detectable color change, although other immobilization means are also contemplated. The present invention provides for the direct detection of the presence of a wide range of analytes by changes in color, including, but not limited to, small molecules, pathogens, bacteria, membrane receptors, membrane fragments, volatile organic compounds (VOCs), enzymes, drugs, antibodies, and other relevant materials. Results can be interpreted by an untrained observer, and the methods can be conducted under ambient conditions, making them amenable to numerous uses including, but not limited to, home testing diagnostics, detection of air-borne or water-borne pathogens for military applications, doctor's office or point of care testing, and many other applications. The present invention provides analyte detecting technology that does not require an energy source and is cost-efficient, stable, accurate, reliable, consistent, and robust and can be produced in a variety of shapes and sizes. These enhanced qualities provide an ideal basis for use in conjunction with fiber optic methods for remote sensing, screening new compound libraries (e.g., drug screens), drug testing, water supply testing, and any area where a quick and accurate calorimetric screen is desired.

Recent research has found that liposomes and other lipid-based materials can perform as sensitive optical sensors for the detection of viruses (see e.g., Reichert et al., J. Am. Chem. Soc. 117: 829 [1995]; Spevak et al., J. Am. Chem. Soc. 115: 1146 [1993]; and Charych et al., Science 261: 585 [1993]). These materials exhibit rapid response times, selectivity, and optical signals that are easily monitored. As free floating aggregates in solution, these lipid-based detectors show promise as simple assay systems. The present invention provides embodiments in which these materials are used immobilized in sol-gel glass, offering the advantages of further chemical and physical stabilization of the material, allowing facile handling, and the opportunity of recovery and reuse. To date, this effort has been frustrated by the difficulty in immobilizing lipid assemblies to surfaces. A few methods have been developed that overcome some of the difficulties by employing polysaccharides and biocompatible acrylate gels to encapsulate liposomes. However, until the development of the present invention, low liposome entrapment volume, the inability to immobilize pre-formed liposomes, and material instability at elevated temperatures were shortcomings yet to be resolved.

The present invention provides a means of immobilizing pre-formed liposomes and other biopolymeric material at low (e.g., 4° C.) to ambient temperature, with high material entrapment volume, in a porous, robust metal oxide gel matrix using the sol-gel method (See generally, Brinker and Scherer, Sol-Gel Science, Academic Press, San Diego [1995]). Prior to the present invention, lipid entrapment in sol-gel material has not previously been reported. The unique properties of sol-gel materials of the present invention such as optical transparency, durability, and tailorable properties (e.g., porosity, surface functionalization, thin films, and bulk materials) provide an ideal material for sensor applications.

Sol-gel encapsulation not only provides an excellent way to immobilize liposomes and other biopolymeric material, but the optical clarity of the metal oxide gel also makes it ideal for optical sensor applications. This unique composite can easily be applied to surfaces and cast into any shape desired, allowing configuration to most any sensor platform. The robust nature of the sol-gel material converts the biopolymeric material based assays into sensor materials that afford good portability, handling, durability, and improved storage life (i.e., shelf life) while maintaining sensitivity. In addition, the metal oxide gel's porous structure and ionic surface can be tailored to provide a primary screening mechanism and preconcentrator for selective recognition and sensing of target analytes. The biopolymeric/sol-gel material is a unique class of organic-inorganic composite that offers high matrix stability against microbial attack, temperature changes, and physical stress as opposed to polysaccharide and acrylate gels. The ambient temperature at which gel formation takes place and the biologically inert metal oxide matrix allows a broad range of biopolymeric material and protein-entrained-biopolymeric material to be immobilized.

Thus, the present invention provides methods and compositions that fulfill many of the goals of the analyte detection field and overcomes many of the disadvantages of currently available technologies (e.g., classical methods, biosensors, and immunassays).

The present invention provides significant advantages over previously used biosensors, as the embodiments of the present invention are not dependent upon transducing technologies. Many proposed biosensors cannot be used because of difficulties in transducing the molecule recognition event into a measurable signal. Additionally, the transducers of currently developed devices add cost, create a requirement for a power source, are more difficult to use by untrained personnel, and are limited in terms of miniaturization and portability. Also, many biosensors do not display the long term stability and robustness of the presently claimed invention.

Immunoassays are far more limited in the range of analytes that they can detect and do not feature the stability and robustness of the presently claimed invention. The inventive constructs and methods can assay very small biological or other molecules for which antibodies cannot be developed. These target materials can include organic solvents or pollutants present at extremely low levels.

Definitions

To facilitate an understanding of the present invention, a number of terms and phrases are defined below:

As used herein, the term "immobilization" refers to the attachment or entrapment, either chemically or otherwise, of material to another entity (e.g., a solid support) in a maimer that restricts the movement of the material.

As used herein, the terms "material" and "materials" refer to, in their broadest sense, any composition of matter.

As used herein, the term "biopolymeric material" refers to materials composed of polymerized biological molecules (e.g., lipids, proteins, carbohydrates, and combinations thereof). Such materials include, but are not limited to, films, vesicles, liposomes, multilayers, aggregates, membranes, and solvated polymers (e.g., polythiophene aggregates such as rods and coils in solvent).

As used herein, the term "biopolymeric films" refers to polymerized organic films that are used in a thin section or in a layer form. Such films can include, but are not limited to, monolayers and bilayers. Biopolymeric films can mimic biological cell membranes (e.g., in their ability to interact with other molecules such as proteins or analytes).

As used herein, the term "sol-gel" refers to preparations composed of porous metal oxide glass structures. Such structures can have biological or other material entrapped within the porous structures. The phrase "sol-gel matrices" refers to the structures comprising the porous metal oxide glass with or without entrapped material. The term "sol-gel material" refers to any material prepared by the sol-gel process including the glass material itself and any entrapped material within the porous structure of the glass. As used herein, the term "sol-gel method" refers to any method that results in the production of porous metal oxide glass. In some embodiments, "sol-gel method" refers to such methods conducted under mild temperature conditions. The terms "sol-gel glass" and "metal oxide glass" refer to glass material prepared by the sol-gel method and include inorganic material or mixed organic/inorganic material. The materials used to produce the glass can include, but are not limited to, aluminates, aluminosilicates, titanates, ormosils (organically modified silanes), and other metal oxides.

As used herein, the term "direct colorimetric detection" refers to the detection of color changes without the aid of an intervening processing step (e.g., conversion of a color change into an electronic signal that is processed by an interpreting device). It is intended that the term encompass visual observing (e.g., observing with the human eye).

As used herein, the term "analytes" refers to any material that is to be analyzed. Such material can include, but is not limited to, molecules, bacteria, compounds, viruses, cells, antibodies, and cell parts.

As used herein, the term "selective binding" refers to the binding of one material to another in a manner dependent upon the presence of a particular molecular structure (i.e., specific binding). For example, a receptor will selectively bind ligands that contain the chemical structures complimentary to the ligand binding site(s).

As used herein, the term "biosensors" refers to any sensor device that is partially or entirely composed of biological molecules. In a traditional sense, the term refers to "an analytical tool or system consisting of an immobilized biological material (such as enzyme, antibody, whole cell, organelle, or combination thereof) in intimate contact with a suitable transducer device which will convert the biochemical signal into a quantifiable electrical signal" (Gronow, Trends Biochem. Sci. 9: 336 [1984]).

As used herein, the term "transducer device" refers to a device that is capable of converting a non-electrical phenomenon into electrical information, and transmitting the information to a device that interprets the electrical signal. Such devices can include, but are not limited to, devices that use photometry, fluorimetry, and chemiluminescence; fiber optics and direct optical sensing (e.g., grating coupler); surface plasmon resonance; potentiometric and amperometric electrodes; field effect transistors; piezoelectric sensing; and surface acoustic wave.

As used herein, the term "miniaturization" refers to a reduction in size, such as the size of a sample to increase utility (e.g., portability, ease of handling, and ease of incorporation into arrays).

As used herein, the term "stability" refers to the ability of a material to withstand deterioration or displacement and to provide reliability and dependability.

As used herein, the term "conformational change" refers to the alteration of the molecular structure of a substance. It is intended that the term encompass the alteration of the structure of a single molecule or molecular aggregate (e.g., the change in structure of polydiacetylene upon interaction with an analyte).

As used herein, the term "small molecules" refers to any molecule with low molecular weight (i.e., less than 10,000 atomic mass units and preferably less than 5,000 atomic mass units) that binds to ligands, interacts with ligands, or interacts with biopolymeric material in a manner that creates a conformational change.

As used herein, the term "pathogen" refers to disease causing organisms, microorganisms, or agents including, but not limited to, viruses, bacteria, parasites (including, but not limited to, organisms within the phyla Protozoa, Platyhelminthes, Aschelminthes, Acanthocephala, and Arthropoda), fungi, and prions.

As used herein, the term "bacteria" and "bacterium" refer to all prokaryotic organisms, including those within all of the phyla in the Kingdom Procaryotae. It is intended that the term encompass all microorganisms considered to be bacteria including Mycoplasma, Chlamydia, Actinomyces, Streptomyces, and Rickettsia. All forms of bacteria are included within this definition including cocci, bacilli, spirochetes, spheroplasts, protoplasts, etc. "Gram negative" and "gram positive" refer to staining patterns obtained with the Gram-staining process which is well known in the art (See e.g., Finegold and Martin, Diagnostic Microbiology, 6th Ed. (1982), CV Mosby St. Louis, pp 13–15).

As used herein, the term "membrane" refers to, in its broadest sense, a thin sheet or layer of material. It is intended that the term encompass all "biomembranes" (i.e., any organic membrane including, but not limited to, plasma membranes, nuclear membranes, organelle membranes, and synthetic membranes). Typically, membranes are composed of lipids, proteins, glycolipids, steroids, sterol and/or other components. As used herein, the term "membrane fragment" refers to any portion or piece of a membrane. The term "polymerized membrane" refers to membranes that have undergone partial or complete polymerization.

As used herein, the term "polymerization" encompasses any process that results in the conversion of small molecular monomers into larger molecules consisting of repeated units.

As used herein, the term "membrane receptors" refers to constituents of membranes that are capable of interacting with other molecules or materials. Such constituents can include, but are not limited to, proteins, lipids, carbohydrates, and combinations thereof.

As used herein, the term "volatile organic compound" or "VOC" refers to organic compounds that are reactive (i.e., evaporate quickly, explosive, corrosive, etc.), and typically are hazardous to human health or the environment above certain concentrations. Examples of VOCs include, but are not limited to, alcohols, benzenes, toluenes, chloroforms, and cyclohexanes.

As used herein, the term "enzyme" refers to molecules or molecule aggregates that are responsible for catalyzing chemical and biological reactions. Such molecules are typically proteins but can also be short peptides, RNAs, or other molecules.

As used herein, the term "drug" refers to a substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology.

As used herein, the term "peptide" refers to any substance composed of two or more amino acids.

As used herein, the term "carbohydrate" refers to a class of molecules including, but not limited to, sugars, starches, cellulose, chitin, glycogen, and similar structures. Carbohydrates can occur as components of glycolipids and glycoproteins.

As used herein, the term "chromophore" refers to molecules or molecular groups responsible for the color of a compound, material, or sample.

As used herein, the term "antigen" refers to any molecule or molecular group that is recognized by at least one antibody. By definition, an antigen must contain at least one epitope (i.e., the specific biochemical unit capable of being recognized by the antibody). The term "immunogen" refers to any molecule, compound, or aggregate that induces the production of antibodies. By definition, an immunogen must contain at least one epitope (i.e., the specific biochemical unit capable of causing an immune response).

As used herein, the term "chelating compound" refers to any compound composed of or containing coordinate links that complete a closed ring structure.

As used herein, the term "molecular recognition complex" refers to any molecule, molecular group, or molecular complex that is capable of recognizing (i.e., specifically interacting with) a molecule.

As used herein, the term "ambient condition" refers to the conditions of the surrounding environment (e.g., the temperature of the room or outdoor environment in which an experiment occurs).

As used herein, the term "room temperature" refers, technically, to temperatures approximately between 20 and 25 degrees centigrade. However, as used generally, it refers to the any ambient temperature within a general area in which an experiment is taking place.

As used herein, the terms "home testing" and "point of care testing" refer to testing that occurs outside of a laboratory environment. Such testing can occur indoors or outdoors at, for example, a private residence, a place of business, public or private land, in a vehicle, under water, as well as at the patient's bedside.

As used herein, the term "lipid" refers to a variety of compounds that are characterized by their solubility in organic solvents. Such compounds include, but are not limited to, fats, waxes, steroids, sterols, glycolipids, glycosphingolipids (including gangliosides), phospholipids, terpenes, fat-soluble vitamins, prostaglandins, carotenes, and chlorophylls. As used herein, the phrase "lipid-based materials" refers to any material that contains lipids.

As used herein, the term "virus" refers to any infectious agent, unable to multiply without a host cell (i.e., agents that are obligate parasites).

As used herein, the phrase "free floating aggregates" refers to aggregates that have not been immobilized.

As used herein, the term "encapsulate" refers to the process of encompassing, encasing, or otherwise associating two or more materials such that the encapsulated material is immobilized within or onto the encapsulating material. For example, the sol-gel process provides a means to encapsulate material into porous sol-gel glass material.

As used herein, the term "entrapment volume" refers to the volume of material encapsulated within a material. For example, the volume of liposome encapsulated within the porous structure of sol-gel glass material is its entrapment volume.

As used herein, the term "optical transparency" refers to the property of matter whereby the matter is capable of transmitting light such that the light can be observed by visual light detectors (e.g., eyes and detection equipment).

As used herein, the term "biologically inert" refers to a property of material whereby the material does not chemically react with biological material.

As used herein, the term "organic solvents" refers to any organic molecules capable of dissolving another substance. Examples include, but are not limited to, chloroform, alcohols, phenols, and ethers.

As used herein, term "nanostructures" refers to microscopic structures, typically measured on a nanometer scale. Such structures include various three-dimensional assemblies, including, but not limited to, liposomes, films, multilayers, braided, lamellar, helical, tubular, and fiber-like shapes, and combinations thereof. Such structures can, in some embodiments, be solvated polymers in aggregate forms such as rods and coils.

As used herein, the term "films" refers to any material deposited or used in a thin section or in a layer form.

As used herein, the term "vesicle" refers to a small enclosed structures. Often the structures are membranes composed of lipids, proteins, glycolipids, steroids or other components associated with membranes. Vesicles can be naturally generated (e.g., the vesicles present in the cytoplasm of cells that transport molecules and partition specific cellular functions) or can be synthetic (e.g., liposomes).

As used herein, the term "liposome" refers to artificially produced spherical lipid complexes that can be induced to segregate out of aqueous media.

As used herein, the term "biopolymeric liposomes" refers to liposomes that are composed entirely, or in part, of biopolymeric material.

As used herein, the term "tubules" refers to materials comprising small hollow cylindrical structures.

As used the term "multilayer" refers to structures comprised of two or more monolayers. The individual monolayers may chemically interact with one another (e.g., through covalent bonding, ionic interactions, van der Waals' interactions, hydrogen bonding, hydrophobic or hydrophilic assembly, and stearic hindrance) to produce a film with novel properties (i.e., properties that are different from those of the monolayers alone).

As used herein, the term "self-assembling monomers" refers to molecules that spontaneously associate to form molecular assemblies. In one sense, this can refer to surfactant molecules that associate to form surfactant molecular assemblies. "Surfactant molecular assemblies" refers to an assembly of surface active agents that contain chemical groups with opposite polarity, form oriented monolayers at phase interfaces, form micelles (colloidal particles in aggregation colloids), and have detergent, foaming, wetting, emulsifying, and dispersing properties.

As used herein, the term "homopolymers" refers to materials comprised of a single type of polymerized molecular species. The phrase "mixed polymers" refers to materials comprised of two or more types of polymerize molecular species.

As used herein, the term "ligands" refers to any ion, molecule, molecular group, or other substance that binds to another entity to form a larger complex. Examples of ligands include, but are not limited to, peptides, carbohydrates, nucleic acids, antibodies, or any organic molecules that bind to receptors.

As used herein, the terms "organic matrix" and "biological matrix" refer to collections of organic molecules that are assembled into a larger multi-molecular structure. Such structures can include, but are not limited to, films, monolayers, and bilayers. As used herein, the term "organic monolayer" refers to a thin film comprised of a single layer of carbon-based molecules. In one embodiment, such monolayers can be comprised of polar molecules whereby the hydrophobic ends all line up at one side of the monolayer. The term "monolayer assemblies" refers to structures comprised of monolayers. The term "organic polymetric matrix" refers to organic matrices whereby some or all of the molecular constituents of the matrix are polymerized.

As used herein, the phrase "head group functionality" refers to the molecular groups present an the ends of molecules (e.g., the carboxylic acid group at the end of fatty acids).

As used herein, the term "hydrophilic head-group" refers to ends of molecules that are substantially attracted to water by chemical interactions including, but not limited to, hydrogen-bonding, van der Waals' forces, ionic interactions, or covalent bonds. As used herein, the term "hydrophobic head-group" refers to ends of molecules that self-associate with other hydrophobic entities, resulting in their exclusion from water.

As used herein, the term "carboxylic acid head groups" refers to organic compounds containing one or more carboxyl (—COOH) groups located at, or near, the end of a molecule. The term carboxylic acid includes carboxyl groups that are either free or exist as salts or esters.

As used herein, the term "detecting head group" refers to the molecular group contained at the end of a molecule that is involved in detecting a moiety (e.g., an analyte).

As used herein, the term "linker" or "spacer molecule" refers to material that links one entity to another. In one sense, a molecule or molecular group can be a linker that is covalent attached two or more other molecules (e.g., linking a ligand group to a self-assembling monomer).

As used herein, the phrase "polymeric assembly surface" refers to polymeric material that provides a surface for the assembly of further material (e.g., a biopolymeric surface of a film or liposome that provides a surface for attachment and assembly of ligands).

As used herein, the phrase "chromatic detection element" refers to material that is capable of providing colorimetric analysis (e.g., polymerized diacetylene).

As used herein, the term "formation support" refers to any device or structure that provides a physical support for the production of material. In some embodiments, the formation support provides a structure for layering and/or compressing films.

As used herein, the term "10,12-pentacosadiynoic acid" refers to the compound with the following chemical formula: $CH_3$—$(CH_2)_{11}$—C≡C—C≡C—$(CH_2)_8$—COOH. The term 5,7-pentacosadiynoic acid" refers to the compound with the formula: $CH_3$—$(CH_2)_{16}$—C≡C—C≡C—$(CH_2)_3$—COOH.

As used herein, the term "diacetylene monomers" refers to single copies of hydrocarbons containing two alkyne linkages (i.e., carbon/carbon triple bonds).

As used herein, the terms "standard trough" and "standard Langmuir-Blodgett trough" refer to a device, usually made of teflon, that is used to produce Langmuir films. The device contains a reservoir that holds an aqueous solution and moveable barriers to compress film material that are layered onto the aqueous solution (See e.g., Roberts, *Langmuir-Blodgett Films*, Plenum, N.Y., [1990]).

As used herein, the term "crystalline morphology" refers to the configuration and structure of crystals that can include, but are not limited to, crystal shape, orientation, texture, and size.

As used herein, the term "domain boundary" refers to the boundaries of an area in which polymerized film molecules are homogeneously oriented. For example, a domain boundary can be the physical structure of periodic, regularly arranged polydiacetylene material (e.g., striations, ridges, and grooves).

As used herein, the term "domain size" refers to the typical length between domain boundaries.

As used the term "conjugated backbone" refers to the ene-yne polymer backbone of p-PCA films that, on a macroscopic scale, appears in the form of physical ridges or striations. The term "polymer backbone axis" refers to an imaginary line that runs parallel to the conjugated backbone. The terms "intrabackbone" and "interbackbone" refer to the regions within a given polymer backbone and between polymer backbones, respectively. The backbones create a series of lines or "linear striations," that extend for distances along the template surface.

As used herein, the term "bond" refers to the linkage between atoms in molecules and between ions and molecules in crystals. The term "single bond" refers to a bond with two electrons occupying the bonding orbital. Single bonds between atoms in molecular notations are represented by a single line drawn between two atoms (e.g., $C_8$-$C_9$). The term "double bond" refers to a bond that shares two electron pairs. Double bonds are stronger than single bonds and are more reactive. The term "triple bond" refers to the sharing of three electron pairs. As used herein, the term "ene-yne" refers to alternating double and triple bonds.

As used the term "absorption" refers, in one sense, to the absorption of light. Light is absorbed if it is not reflected from or transmitted through a sample. Samples that appear colored have selectively absorbed all wavelengths of white light except for those corresponding to the visible colors that are seen.

As used herein, the term "spectrum" refers to the distribution of light energies arranged in order of wavelength.

As used the term "visible spectrum" refers to light radiation that contains wavelengths from approximately 360 nm to approximately 800 nm.

As used herein, the term "ultraviolet irradiation" refers to exposure to radiation with wavelengths less than that of visible light (i.e., less than 360 nM) but greater than that of X-rays (i.e., greater than 0.1 nM). Ultraviolet radiation possesses greater energy than visible light and is therefore, more effective at inducing photochemical reactions.

As used herein, the term "chromatic transition" refers to the changes of molecules or material that result in an alteration of visible light absorption. In some embodiments, chromatic transition refers to the change in light absorption of a sample, whereby there is a detectable color change associated with the transition. This detection can be accomplished through various means including, but not limited to, visual observation and spectrophotometry.

As used herein, the term "thermnochromic transition" refers to a chromatic transition that is initiated by a change in temperature.

As used herein, the term "solid support" refers to a solid object or surface upon which a sample is layered or attached. "Hydrophobized solid support" refers to a solid support that has been chemically treated or generated so that it attracts hydrophobic entities and repels water.

As used herein, the phrase "solid sensor platforms" refers to any solid support used for immobilizing sensor material.

As used herein, the term "film-ambient interface" refers to a film surface exposed to the ambient environment or atmosphere (i.e., not the surface that is in contact with a solid support).

As used herein, the term "formation solvent" refers to any medium, although typically a volatile organic solvent, used to solubilize and distribute material to a desired location (e.g., to a surface for producing a film or to a drying receptacle to deposit liposome material for drying).

As used herein, the term "micelle" refers to a particle of colloidal size that has a hydrophilic exterior and hydrophobic interior.

As used herein, the term "topochemical reaction" refers to reactions that occur within a specific place (e.g., within a specific portion of a molecule or a reaction that only occurs when a certain molecular configuration is present).

As used herein, the term "molding structure" refers to a solid support used as a template to design material into desired shapes and sizes.

As used herein, the terms "array" and "patterned array" refer to an arrangement of elements (i.e., entities) into a material or device. For example, combining sections of sol-gel material, that have different biopolymeric samples encapsulated, into an analyte-detecting device would constitute an array.

As used herein the term "interferants" refers to entities present in an analyte sample that are not the analyte to be detected and that, preferably, a detection device will not identify, or would differentiate from the analyte(s) of interest.

As used herein, the term "badge" refers to any device that is portable and can be carried or worn by an individual working in an analyte detecting environment.

As used herein, the term "halogenation" refers to the process of incorporating or the degree of incorporation of halogens (i.e., the elements fluorine, chlorine, bromine, iodine and astatine) into a molecule.

As used herein, the term "aromaticity" refers to the presence aromatic groups (i.e., six carbon rings and derivatives thereof) in a molecule.

As used herein, the phrase "water-immiscible solvents" refers to solvents that do not dissolve in water in all proportions. The phrase "water-miscible solvents" refers to solvents that dissolve in water in all proportions.

As used herein, the terms "positive," "negative," and "zwitterionic charge" refer to molecules or molecular groups that contain a net positive, negative, or neutral charge, respectively. Zwitterionic entities contain both positively and negatively charged atoms or groups whose charges cancel.

As used herein, the term "biological organisms" refers to any carbon-based life forms.

As used herein, the term "in situ" refers to processes, events, objects, or information that are present or take place within the context of their natural environment. For example, in situ microscopy refers to the analysis of material in its natural (i.e., not sectioned, fixed, or otherwise altered) form.

As used the term "aqueous" refers to a liquid mixture containing water, among other components.

As used herein, the term "solid-state" refers to reactions involving one or more rigid or solid-like compounds.

As used herein, the term "regularly packed" refers to the periodic arrangement of molecules within a compressed film.

As used herein, the term "filtration" refers to the process of separating samples from one another. In one embodiment, filtration refers to the separation of solids from liquids or gasses by the use of a membrane or medium.

As used herein, the term "sample" is used in its broadest sense. In one sense it can refer to a crystallized product. In another sense, it is meant to include a specimen or culture; on the other hand, it is meant to include biological and environmental samples. Biological samples include blood products, such as plasma, serum and the like. Biological samples may be animal, including human, fluid, solid or tissue. Environmental samples include environmental material such as surface matter, soil, water, crystals and industrial samples. These examples are not to be construed as limiting the sample types applicable to the present invention.

DETAILED DESCRIPTION OF THE INVENTION

The presently claimed invention comprises methods and compositions related to biopolymeric material encapsulated in sol-gel and immobilized on other solid supports, for the calorimetric detection of analytes. Biopolymeric materials including, but not limited to, films, vesicles, tubules, and multilayered structures are incorporated into sol-gel matrices. The biopolymeric materials contain polymerized self-assembling monomers that undergo conformational changes and chromatic transitions upon analyte exposure. The analytes either interact directly with the monomers or with ligands that are linked to or associated with the monomers. The entrapment in sol-gel provides stability, robustness, and manipulability to the biopolymeric sensor material. With certain biopolymeric material, a color transition occurs upon analyte binding that can be viewed by simple visual observation or, if desired, by color sensing equipment. The methods and compositions of the presently claimed invention find use in a broad range of analyte detection circumstances and are particularly amenable to situations where simple, rapid, accurate, and cost-efficient detection is required.

In certain embodiments, the present invention contemplates a variety of self-assembling monomers that are suitable for formation into biopolymeric materials. Such monomers include, but are not limited to, acetylenes, diacetylenes (e.g., 5,7-docosadiynoic acid, 5,7-pentacosadiynoic acid, and 10,12-pentacosadiynoic acid), alkenes, thiophenes, polythiophenes, imides, acrylamides, methacrylates, vinylether, malic anhydride, urethanes, allylamines, siloxanes anilines, pyrroles, and vinylpyridinium. Lipids containing these groups can be homopolymers or mixed polymers. Furthermore, monomers with a variety of head groups are contemplated including, but not limited to carboxylic acid, hydroxyl groups, primary amine functionalities, amino acid derivatives, and hydrophobic groups.

Ligands can be linked by a linking arm to the self-assembling monomers, can be directly linked to the monomers, can be incorporated into the matrix during the polymerization process, or can be attached to the matrix following polymerization (e.g., by linking ligands to matrix constituents that contain head groups which bind to the ligands). The ligand group of the present invention can be of a wide variety of materials. The main criteria is that the ligand have an affinity for the analyte of choice. Appropriate ligands include, but are not limited to, peptides, carbohydrates, nucleic acids, biotin, drugs, chromophores, antigens, chelating compounds, molecular recognition complexes, ionic groups, polymerizable groups, dinitrophenols, linker groups, electron donor or acceptor groups, hydrophobic groups, hydrophilic groups, antibodies, or any organic molecules that bind to receptors. The biopolymeric material can be composed of combinations of ligand-linked and unlinked monomers to optimize the desired calorimetric response (e.g., 5% ligand-linked DCDA and 95% DCDA). Additionally, multiple ligands can be incorporated into a single biopolymeric matrix.

In some embodiments, ligands are incorporated to detect a variety of bacteria and pathogens including, but not limited to, sialic acid to detect HIV (Wies et al., Nature 333: 426 [1988]), influenza (White et al., Cell 56: 725 [1989]), chlamydia (Infect. Imm. 57: 2378 [1989]), reovirus, *Streptococcus suis*, Salmonella, Sendai virus, mumps, newcastle, myxovirus, and *Neisseria meningitidis*; 9-OAC sialic acid to detect coronavirus, encephalomyelitis virus, and rotavirus; non-sialic acid glycoproteins to detect cytomegalovirus (Virology 176: 337 [1990]) and measles virus (Virology 172: 386 [1989]); CD4 (Khatzman et al., Nature 312: 763 [1985]), vasoactive intestinal peptide (Sacerdote et al., J. of Neuroscience Research 18: 102 [1987]), and peptide T (Ruff et al., FEBS Letters 211: 17 [1987]) to detect HIV; epidermal growth factor to detect vaccinia (Epstein et al., Nature 318: 663 [1985]); acetylcholine receptor to detect rabies (Lentz et al., Science 215: 182 [1982]); Cd3 complement receptor to detect Epstein-Barr virus (Carel et al., J. Biol. Chem. 265: 12293 [1990]); β-adrenergic receptor to detect rheovirus (Co et al., Proc. Natl. Acad. Sci. 82: 1494 [1985]); ICAM-1 (Marlin et al., Nature 344: 70 [1990]), N-CAM, and myelin-associated glycoprotein MAb (Shephey et al., Proc. Natl. Acad. Sci. 85: 7743 [1988]) to detect rhinovirus; polio virus receptor to detect polio virus (Mendelsohn et al., Cell 56: 855 [1989]); fibroblast growth factor receptor to detect herpesvirus (Kaner et al., Science 248: 1410 [1990]); oligomannose to detect *Escherichia coli*; ganglioside $G_{M1}$ to detect *Neisseria meningitidis*; and antibodies to detect a broad variety of pathogens (e.g., *Neisseria gonorrhoeae, V. vulnificus, V. parahaemolyticus, V. cholerae*, and *V. alginolyticus*).

In some embodiments, the self-assembling monomers are not associated with ligands, but are directly assembled, polymerized, and entrapped into sol-gel. Such biopolymeric materials find use in the detection of certain classes of analytes including, but not limited to, volatile organic compounds (VOCs).

Production of Biopolymeric Material

In some embodiments, the present invention provides biopolymeric material composed of polymerized monomers whose head groups are linked to a ligand through a linear structural linker. For example, FIG. 1 provides a schematic depiction of one embodiment of the present invention. Compound 1 shows a receptor-binding ligand (sialic acid) attached to one terminal end of a spacer molecule. The second terminal end of the spacer molecule is attached to one of several monomers (10,12-pentacosadiynoic acid, i.e., compound 2) that have been polymerized so as to form a chromatic detection element. These materials are then agitated while polymerization occurs, causing the formation of the polymeric structures, including, but not limited to, films, liposomes, vesicles, tubules, multilayered structures, and other nanostructures.

In some embodiments, the biopolymeric material used in the presently claimed invention comprises a biopolymeric film. As described in Example 1, film was prepared by layering the desired matrix-forming material (e.g., self-assembling organic monomers) onto a formation support. In preferred embodiments, the formation support was a standard Langmuir-Blodgett trough and the matrix-forming material was layered onto an aqueous surface created by filling the trough with an aqueous solution. The material was then compressed and polymerized to form a biopolymeric film. In preferred embodiments, the compression was conducted in a standard Langmuir-Blodgett trough using moveable barriers to compress the matrix-forming material. Compression was carried out until a tight-packed monolayer of the matrix-forming material was formed.

As described in Example 1, in some embodiments, the matrix-forming material, located within the formation support, was polymerized by ultra-violet irradiation. All methods of polymerization are contemplated by the present invention and include, but are not limited to, gamma irradiation, x-ray irradiation, and electron beam exposure.

In preferred embodiments, the biopolymeric films comprise polymerized Langmuir-Schaefer films of 5,7-docosadiynoic acid (DCDA) linked to or associated with the desired ligand, although other PCAs are contemplated, including, but not limited to, 5,7-pentacosadiynoic acid (p-PCA) and 10,12-p-PCA. These films produce a visible color transition when exposed to the appropriate analyte. As described in Example 1, the films were generated by spreading and compressing 5,7-DCDA and the desired ligand or ligand-derived 5,7-DCDA (i.e., 5,7-DCDA chemically linked to a ligand) on the surface of a formation support. In preferred embodiments, the formation support is a standard Langmuir-Blodgett trough, with the materials layered onto an aqueous surface created by filling the trough with an aqueous solution, although any formation support that facilitates the spreading and compressing of the film is contemplated by the present invention.

The diacetylene monomers (DA) were polymerized to polydiacetylene (p-PDA or PDA) using ultraviolet irradiation. In preferred embodiments, the ultraviolet radiation source is kept sufficiently far from the film to avoid causing heat damage to the film. The crystalline morphology of the polymerized film can be readily observed between crossed polarizers in an optical microscope, although this step is not required by the present invention. For p-PCA, the domain size varied up to 1 mm, although it is contemplated that domains as large as approximately 3 mm can be grown (See e.g., Day and Lando, Macromolecules 13: 1478 [1980]). The conjugated backbone of alternating double and triple bonds (i.e., ene-yne) that was generated, gave rise to intense absorptions in the visible spectrum and led to a distinct blue appearance of the polymerized film.

In certain embodiments the visibly blue films were then transferred to hydrophobized solid supports, such that the carboxylic acid head groups were exposed at the film-ambient interface (Charych et al., Science 261: 585 [1993]) to undergo further analysis, although the method of the present invention does not require this step. Linear striations typical of p-PDA films can be observed in the polarizing optical microscope. The material may also be characterized using atomic force microscopy.

In preferred embodiments, the biopolymeric material used in the presently claimed invention comprises biopolymeric liposomes. Liposomes were prepared using a probe sonication method (New, Liposomes: *A Practical Approach*, Oxford University Press, Oxford, pp 33–104 [1990]), although any method that generates liposomes is contemplated. Self-assembling monomers, either alone, or associated with a desired ligand, were dried to remove the formation solvents and resuspended in deionized water. The suspension was probe sonicated and polymerized. The resulting liposome solution contained biopolymeric liposomes.

In some embodiments, the sonicated solution was polymerized by ultra-violet irradiation using a hand-held lamp.

In preferred embodiments. the biopolymeric liposomes comprised 5,7-DCDA alone or mixed with 5,7-DCDA linked to or associated with the desired ligand, although other self-assembling monomers are contemplated including, but not limited to, 5,7-PCA and 10,12-PCA. During polymerization, the appearance of colored polymer provides a sensitive and simple test of molecular order in the self-assembled nanostructure. "Looser" structures such as micelles do not form the conjugated polymer, possibly due to the topochemical nature of the polymerization reaction. The conjugated ene-yne backbone of polydiacetylene liposomes resulted in the appearance of a deep blue/purple solution.

In other embodiments, it is contemplated that variations in the heating and cooling rates, agitation methods, and materials of the biopolymeric material will provide other nanostructures. Such nanostructures include, but are not limited to, multilayers, braided, lamellar, helical, tubular, and fiber-like shapes, and combinations thereof. Such structures can, in some embodiments, be solvated polymers in aggregate forms such as rods and coils. For example, it has been shown that the chain length of the monomers effects the type of aggregate that forms in solution (Okahata and Kunitake, J. Am. Chem. Soc. 101: 5231 [1979]).

Entrapment of Biopolymeric Material by the Sol-Gel Method

While the sol-gel process has been used for entrapping organic molecules such as dyes and biomolecules in silica gels (See e.g., Avnir, Accounts Chem. Res. 28: 328 [1995]; Yamanaka et al., Am. Chem. Soc. 117: 9095 [1995]; Miller et al., Non-Cryst. Solids 202: 279 [1996]; and Dave et al., Anal. Chem. 66: 1120A [1994]), prior to the development of the present invention, immobilization of self-organized molecular aggregates (e.g., biopolymeric material, self-assembling monomer aggregates, and liposomes) was not realized in sol-gel materials.

Embodiments of the presently claimed invention provide for the successful immobilization of spherical, bilayer lipid aggregates, and liposomes using an aqueous sol-gel procedure. These molecular structures, and particularly liposomes, composed of biological or biomimetic (i.e., mimics nature) lipids, are fairly robust under aqueous conditions and ambient temperatures but can easily degrade in the presence of organic solvents and high temperatures. The sol-gel process provides a facile method of immobilizing molecular aggregates with no detectable structure modification, creating robust structures that are easily fabricated into any desired size or shape.

The silica sol-gel material was prepared by sonicating tetramethylorthosilicate, water, and hydrochloric acid under chilled conditions until a single phased solution was obtained. The use of metal oxides, other than tetramethylorthosiliate, are contemplated by the present invention, so long as they facilitate the entrapment and form substantially transparent glass material. Such metal oxides include, but are not limited to, silicates, titanates, aluminates, ormosils, and others. Buffer was then added to the acidic solution under cooling conditions. The biopolymeric materials, generated as described above, were mixed into the buffered sol solution. This composite was poured into a desired molding structure and allowed to gel at ambient temperatures. It is not intended that the present invention be limited by the type of molding structure used, as it is contemplated that a variety of structures can be applied to generate gels of any desired size and shape including, but not limited to, cuvettes, flat surfaces for generating thin films, plastic, ceramic, or metal moldings to generate badges, etc. It is not intended that the present invention be limited to gelation at ambient temperatures, as any temperature range that facilitates the production of functional analyte-detecting gels is contemplated.

Figure 2:
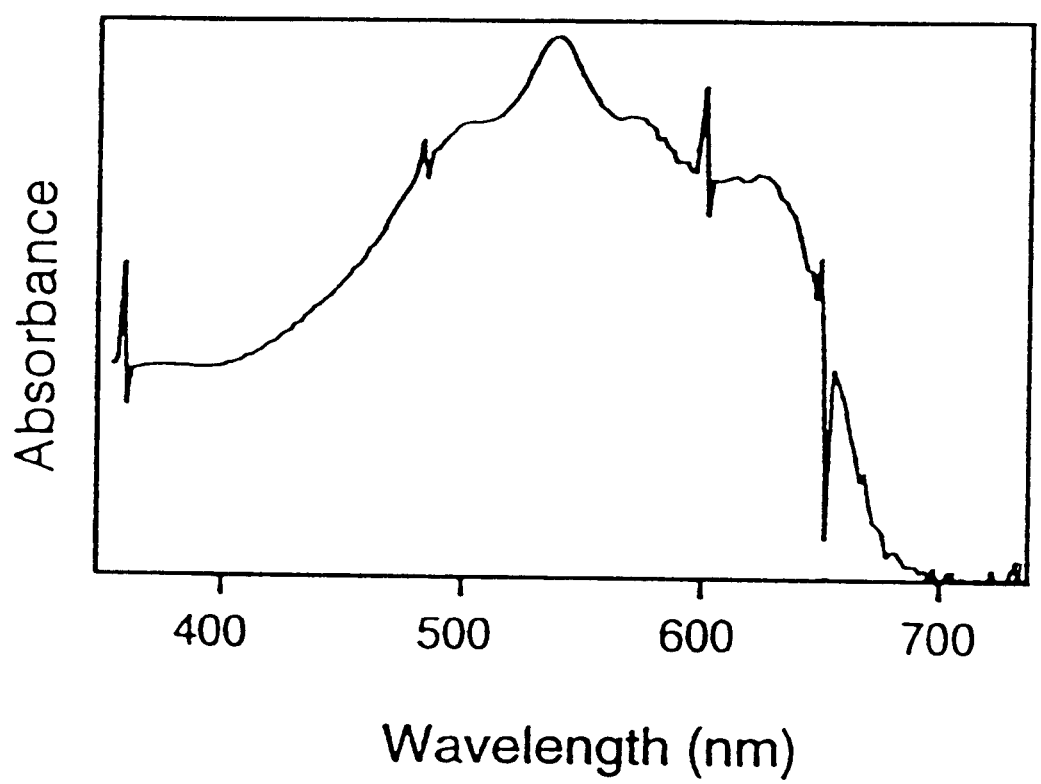
FIG. 2 shows a visible absorption spectrum of "blue phase" DCDA liposomes entrapped in sol-gel glass.
Figure 3:
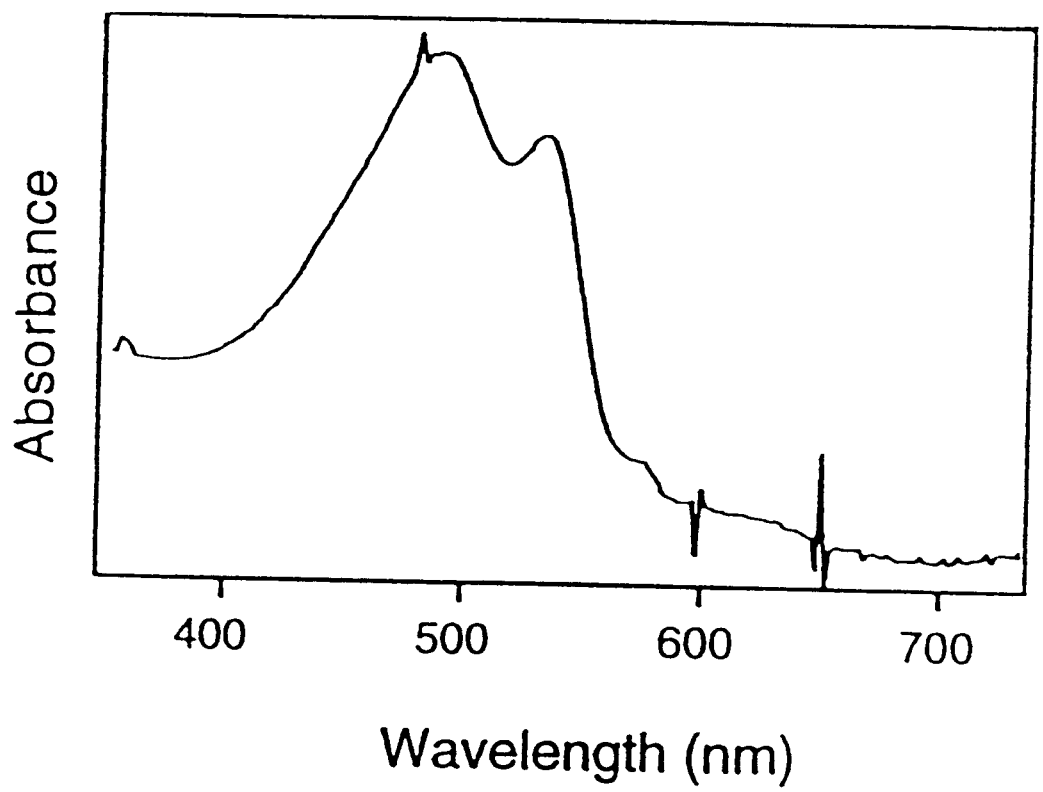
FIG. 3 shows a visible absorption spectrum of "red phase" DCDA liposomes entrapped in sol-gel glass.

In one embodiment, DCDA liposomes were incorporated into sol-gel glass, although incorporation of any biopolymeric structure is contemplated by the present invention. Following the sol-gel procedure as described above, gelation occurred within a few minutes, producing gels with a violet color. The visible absorption spectra of the polydiacetylene liposomes, as shown in FIG. 2, was unaltered in the sol-gel matrix compared to liposomes in solution. Following heating of the liposomes to 55° C., a blue to red thermochromic transition occurred that was characteristic of polydiacetylene materials. The blue to red phase materials were similarly unchanged in the sol-gel state compared to solution as shown in the spectrum in FIG. 3. Thus, the presently claimed invention provides a sol-gel matrix that is compatible with the most fragile of the biopolymeric structures (i.e., liposomes) and maintains those physical properties that were observed in bulk solution.

Colorimetric Detection

The sol-gel materials containing the biopolymeric material can be used as colorimetric analyte detectors. Various spectral changes to the sol-gel entrapped biopolymeric materials can be used to detect the presence or absence of the target analytes. Means of amplifying the spectral signal well known in the art, such as scintillators, can also be employed to detect levels of analyte. Because of the nature of the signal, it is contemplated that the detection methods be automated, if desired. However, automation is not required to practice the present invention.

In preferred embodiments of the presently claimed invention, a color shift was observed simply by visual observation. Thus, the present invention may be easily used by an untrained observer such as an at-home user.

In alternative embodiments, spectral test equipment well known in the art is employed to detect changes in spectral qualities beyond the limits of simple visual observation, including optical density to a particular illuminating light wavelength. For example, using a spectrometer, the spectrum of the material was measured before and after analyte introduction, and the colorimetric response (%CR) was measured. The visible absorption spectrum of the material prior to analyte exposure was measured as $B_o=I_x/(I_y+I_x)$ where "B" represents the percentage of a given color phase at wavelength $I_x$ compared to a reference wavelength $I_y$. The spectrum was then taken following analyte exposure and a similar calculation was made to determine the $B_{final}$. The colorimetric response was calculated as $\%CR=[(B_o-B_{final})/B_o]\times 100\%$.

Additionally, the presently claimed invention can be, if desired, attached to a transducer device. The association of self-assembled monomer materials with transducers has been described using optical fibers (See e.g., Beswick and Pitt, J. Colloid Interface Sci. 124: 146 [1988]; and Zhao and Reichert, Langmuir 8: 2785 [1992]), quartz oscillators (See e.g., Furuki and Pu, Thin Solid Films 210: 471 [1992]; and Kepley et al., Anal. Chem. 64: 3191 [1992]), or electrode surfaces (See e.g., Miyasaka et al., Chem. Lett., p. 627 [1990]; and Bilewicz and Majda, Langmuir 7: 2794 [1991]). However, unlike these examples, the present invention provides a uniquely stable and robust material that is easily associated with a transducing device. Furthermore, the embodiments of the present invention provide a double-check by observation of color change in the material.

Analyte Detection

The sol-gel entrapped biopolymeric materials created by the methods of the presently claimed invention can be used to detect a large variety of analytes including, but not limited to, small molecules, pathogens, bacteria, membrane receptors, membrane fragments, volatile organic compounds (VOCs), enzymes, drugs, antibodies, and other relevant materials by the observation of color changes that occur upon analyte binding. The presently claimed invention provides very mild testing conditions, providing the ability to detect small biomolecules in a near natural state and avoiding the risks associated with modification or degradation of the analyte.

Certain embodiments of the presently claimed invention contemplate the generation of a large palette of polymerizable lipids with different headgroup chemistries within a single device to increase selectivity, an important factor in the present invention. In one embodiment, lipid-polymer sensors entrapped in sol-gel using an array format (or an "optical nose," by analogy to the pattern recognition capabilities of the mammalian nose) can be used. By using the array format, several advantages can be realized that overcome the shortcomings of a single sensor approach. These include the ability to use partially selective sensors and to measure multicomponent samples. This offers the possibility of sensing a specific analyte in the presence of an interfering background, or to monitor two or more analytes of interest at the same time. The sensitivities of a given lipid to a given solvent can be determined in order to generate identifiable fingerprints characteristic of each solvent. For example, the lipid-polymer film of p-PDA derivative A may convert completely to an orange phase in the presence of benzene (%CR=100), while p-PDA derivative B may have a %CR of 70 giving rise to a pink color, and p-PDA derivative C may have a %CR of 40 yielding a purple color and p-PDA derivative D may not change at all (i.e., therefore, remains blue/purple). The response fingerprint orange/pink/purple/blue-purple would indicate the presence of benzene. Clearly, the higher the number of elements in the array, the greater the chance of a positive identification for a given analyte. The use of sol-gel entrapped biopolymeric material facilitates the generation of such arrays, as gel sections of any desired size and shape can be created and incorporated into a small, easily read and interpretable device.

In other embodiments, arrays of biopolymeric material can be immobilized on a variety of solid supports, including, but not limited to, cellulose, nitrocellulose, and filter paper. For example, the liposome embodiment of the present invention has been loaded into the ink cartridge of a ink jet printer and used to print biopolymeric liposome material onto paper as though it were ink. The liposome material present on the paper maintained its colorimetric properties. This embodiment demonstrates the ease with which patterned arrays can be generated into any desired shape and size. By using multiple cartridges (e.g., using a color printer), patterned arrays can be generated with multiple biopolymeric materials.

Figure 4:
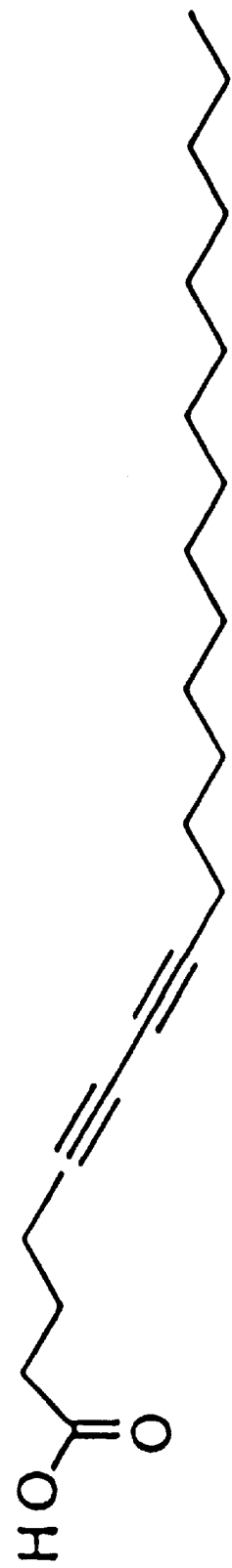
FIG. 4 shows a diagram of PDA with alterations in the position of the diacetylene group from 10,12 to 5,7-pentacosadiynoic acid.

The presently claimed invention further contemplates the optimization of the biopolymeric material to maximize response to given analytes. Although it is not necessary to understand the mechanism in order to use the present invention, and it is not intended that the present invention be so limited, it is contemplated that the chemistry of the particular lipid used in the biopolymeric material plays a critical role in increasing or decreasing the sensitivity of the colorimetric transition. For example, a positional variation of the chromophoric polymer backbone can alter sensitivity to a given analyte. This may be accomplished by moving the diacetylene group closer to the interfacial region as illustrated in FIG. 4 showing 5,7-pentacosadiynoic acid (as opposed to 10,12-pentacosadiynoic acid). In addition, shorter or longer chain lengths of PDA were shown to have an effect on the analyte permeation due to changes in packing. In some embodiments, diacetylene containing from 8–28 carbons was used, although shorter and longer chain lengths are contemplated by the present invention. In other embodiments, the position of the diacetylene group can range from 3–16 carbons away from either end of the molecule, although other locations are also contemplated by the present invention.

Additionally, it is contemplated that sol gel prepared materials of various thicknesses will possess unique sensitivities to analytes. Thicker films have a higher surface to volume ratio and would therefore require a higher concentration of analyte to trigger the chromatic transition. In certain cases, it may be desirable to have a sensor that is less sensitive. This will prevent "false-triggering" in the presence of low levels of analytes where such levels are not relevant (e.g., safe levels of VOCs). Thus, the sensor will be fine-tuned to only trigger at or above pre-designated levels of the analyte.

Furthermore, the gelling conditions of the sol-gel preparation can be optimized by varying gelling temperatures, gel materials, and drying conditions to generate material with desired pore sizes. Varying the crosslink density of the material also provides control over pore size. Pore sizes from nanometers to hundreds of nanometers or greater are contemplated by the present invention. Some gels allow size-selective screening of undesired material while maintaining analyte access to the ligand. Also, the sol-gel technique allows structures to be formed that can be molded into any desirable shape, including, but not limited to, cartridges, coatings, monoliths, powders, and fibers.

Sensitivity can also be enhanced by coupling the lipid-polymer to a photoelectric device, calorimeter, or fiber optic tip that can read at two or more specific wavelengths. Also, the device can be linked to an alternative signalling device such as a sounding alarm or vibration to provide simple interpretation of the signal.

DESCRIPTION OF PREFERRED EMBODIMENTS

Specific applications of the presently claimed invention are described below to illustrate the broad applicability of the invention to a range of analyte detection systems and to demonstrate its specificity, and ease of use. These examples are intended to merely illustrate the broad applicability of the present invention. It is not intended that the present invention be limited to these particular embodiments.

A. Detection of Influenza Virus

To impart specificity, biological ligand molecules were incorporated into the matrix lipid. For example, a lipophilic derivative of the carbohydrate sialic acid was used to specifically bind influenza virus. Sialic acid also has the capability of detecting other analytes including, but not limited to, HIV, influenza, chlamydia, reovirus, *Streptococcus suis*, Salmonella, Sendai virus, mumps, newcastle, myxovirus, and *Neisseria meningitidis*.

The presently claimed invention provides superior means of detecting influenza compared to currently available technology. Immunological assays are limited because of the antigenic shift and drift exhibited by the virus. The presently claimed invention detects all varieties of influenza and thus a determination of a patient's exposure to influenza will be definitive, and not limited to a particular strain. Indeed, even newly evolved, uncharacterized influenza strains can be detected.

In some embodiments of the presently claimed invention, sialic acid coated polydiacetylene liposome materials were successfully immobilized in a silicate matrix via the sol-gel method, to provide sensor materials that offered optical clarity and were robust and easily handled. The mild processing conditions allowed quantitative entrapment of pre-formed liposomes without modification of the aggregate structure. Lipid extraction studies of immobilized non-polymerized liposomes showed no lipid leakage in aqueous solution over a period of three months. Entrapped sialic acid coated polydiacetylene liposomes responded with calorimetric signaling to influenza virus X31. The successful transport of the virus (50–100 nm diameter) revealed a large pore diameter of the gel connecting the liposome to the bulk solution. The porous and durable silicate matrix additionally provided a protective barrier to biological (e.g., bacterial and fungal) attack and allowed facile recycling of the liposome sensor.

Figure 5:
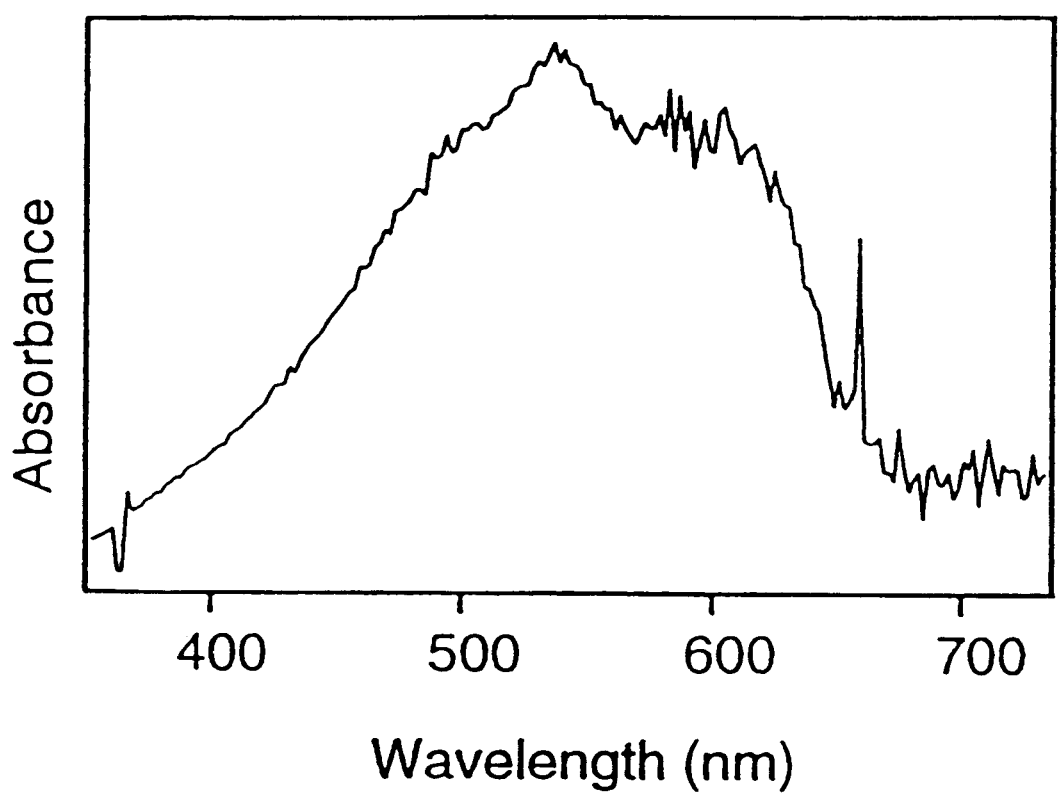
FIG. 5 shows a visible absorption spectrum of "blue phase," sialic acid-linked DCDA liposomes entrapped in sol-gel glass.

The blue to red transition of the polymerized DCDA-containing liposomes was used as a method of detecting the presence of virus particles. It was previously shown that polymerized liposomes functionalized with sialic acid lipid analogs can bind to influenza virus (Charych et al., Science 261: 585 [1993]). Hemagglutinin, the surface lectin of the influenza virus binds to terminal $\alpha$-glycosides of sialic acid on cell surface glycoproteins and glycolipids (Paulson, *The Receptors*, Academic Press, New York, Vol. 2, pp 131–219 [1985]). The purple color of liposomes containing 5% sialic acid-linked PDA was retained after encapsulation in the sol-gel matrix prepared as 1–2 mm thick monoliths as shown in the spectrum in FIG. 5. However, after prolonged incubation with influenza virus X31, the color gradually changed to the red phase as shown in spectrum in FIG. 6. The color change was slower compared to the corresponding experiment in solution (i.e., the experiment with liposomes not immobilized in sol-gel glass). The large steric size of these negatively charged virus particles (50–100 nm diameter) may significantly inhibit their diffusion through the porous gel as illustrated in FIG. 7. However, an understanding of this mechanism is not required in order to use the present invention. Nonetheless, their ability to reach the liposomes provided some insight into the maximum size of the gel pores. Bacterial and fungal attack on the liposomes, observed in solution and with agar entrapment within days of preparation (e.g., colony growth), was not observed over several months where encapsulated according to the present invention. The pore size of the gel likely provided a level of selectivity in these sensor materials, screening out larger interferants, such as bacterial cells (micron size), while allowing selective permeation of smaller agents, such as viruses (tens of nanometers). It is contemplated that by altering the gelling conditions, the pore sizes can be controlled to optimally allow interaction of a given ligand with a variety of differently sized analytes with controllable response times.

In other embodiments, the polymerization of the biopolymeric material was conducted for varying lengths of time to produce different color patterns. Ultraviolet irradiation of sialic acid-linked PCA liposomes for about 5–10 minutes resulted in the formation of the deep blue color as described above. Irradiation for 10–30 minutes yielded a solution with a purple color. When influenza virus was added to the liposomes, a pink or orange color developed from the blue and purple solutions, respectively.

It is also contemplated that the influenza virus detection system include additional ligands that recognize and differentiate influenza strains or serotypes from one another and from other pathogens.

B. Detection of Other Pathogens

The present invention may also be used to detect a variety of other pathogens. Ligands, specific for a large number of pathogens (e.g., carbohydrates, proteins, and antibodies) can be incorporated into the biopolymeric material using routine chemical synthesis methods known in the art (e.g., the latex bead industries have demonstrated synthesis procedures for the attachment of large varieties of chemical groups onto synthetic materials). Some of the examples of pathogen detection systems are presented below to demonstrate the variety of methods that can be applied using the present invention and to demonstrate the broad detecting capabilities of single ligand species (e.g., sialic acid).

The sialic acid derivated material of the present invention has been used to detect the presence of parasites such as Plasmodium (i.e., the etiologic agent that causes malaria). In these embodiments, the genetically conserved host binding site was utilized. PDA films containing sialic acid as described above were exposed to solutions containing malaria parasites and erythrocytes. After overnight exposure to the paracites, the films became pink in color. The color response (CR) in each case was nearly 100%. It is contemplated that the system be used in conjunction with other testing material (e.g., arrays of biopolymeric material with various ligands) to identify and differentiate the presence of particularly virulent species or strains of Plasmodium (e.g., *P. falciparum*) or other pathogens.

In another embodiment, a ligand (i.e., ganglioside $G_{M1}$) was directly incorporated into the biopolymeric matrix as described in Example 3 (i.e., it was not covalently linked to the diacetylene matrix material). Biopolymeric liposomes of such material calorimetrically detected the presence of cholera toxin as shown in FIG. 12. In this figure, A) and B) show visible absorption spectra of the material before and after exposure to cholera toxin, respectively.

In yet other embodiments, antibodies were used as ligands to detect the presence of *Neisseria gonorrhoeae* and *Vibrio vulnificus*. The incorporation of the antibodies into the biopolymeric material is described in Example 3.

As is clear from these examples, the present invention provides a variety of means to detect a broad range of pathogens, including bacteria, viruses, and paracites.

C. Volatile Organic Compound Detection

Certain embodiments of the presently claimed invention provide means to calorimetrically detect volatile organic compounds (VOCs). Most of the current methods of VOC detection require that samples be taken to laboratory facilities where they are analyzed by gas chromatography/mass spectroscopy. Some of the on-site methodologies require large, bulky pieces of equipment such as that used in spectroscopic analysis. While these methods are excellent for providing quantitation and identification of the contaminant, they cannot ensure the safety of the individual worker. In one embodiment, the present invention provides a badge containing sol-gel entrapped biopolymeric material that signals the presence of harmful VOCs and provides maximum workplace safety within areas that contain VOCs. The badge is easy and simple to read and requires no expertise to analyze on the part of the wearer. The color change of the badge signals the individual to take appropriate action. The badges reduce costs and improve the efficiency of environmental management and restoration actions, significantly reducing down-time due to worker illness by preventing over-exposure to potentially harmful substances.

Two main approaches toward VOC detection have been adopted by various groups. The first involves traditional analytical techniques such as GC/MS that have been modified for VOC detection (i.e., an instrument-based approach) (Karpe et al., J. Chromatography A 708: 105 [1995]). However, these methods are expensive, complicated, and do not lend themselves to field or home use. The second involves the coupling of lipid membranes to detector surface (s) (i.e., an organic-device approach). In the past decade, several sensor devices that involve the coating of a piezoclectric mass balance with an organic film have been investigated. Because of the non-selective nature of the coating, these have been investigated in an array. These sensors, such as the quartz crystal microbalance (QCM) and the surface acoustic wave (SAW) devices (See e.g., Rose-Pehrsson et al., Anal. Chem. 60: 2801 [1988]), have linear frequency changes with applied mass. By applying a polymer or other coating to the crystal, a sensor based on the QCM or SAW is constructed. The complex electronics involved in the use of SAW, QCM, and electrode based systems makes these approaches less amenable to use as personal safety devices.

The present invention differs from these methods in that signal transduction is an integral part of the organic layer structure rather than signal transduction to an electronic device. In addition, embodiments of the present invention facilitate optical detection of the signal rather than electronic detection. Furthermore, the present invention provides flexibility in material design, allowing easy immobilization into a small cartridge (e.g., a badge) rather than being burdened with the need for electronic equipment.

In some embodiments of the present invention, surfactant lipid molecules are utilized. The use of surfactant lipid molecules on substrate devices allows a patterned response to a given VOC that depends on the chemical nature of the lipid molecule and the particular VOC. In these embodiments, the advantages of using surfactant molecules are exploited in order to construct the device through molecular self-assembly. In aqueous solution, surfactant molecules spontaneously assemble into micelles, vesicles, bilayer sheets, or thin films by a process that is entropically driven. Furthermore, the sol-gel entrapped materials add robustness and stability. The presently claimed invention offers the added benefit of imparting color to the lipid device.

Figure 8:
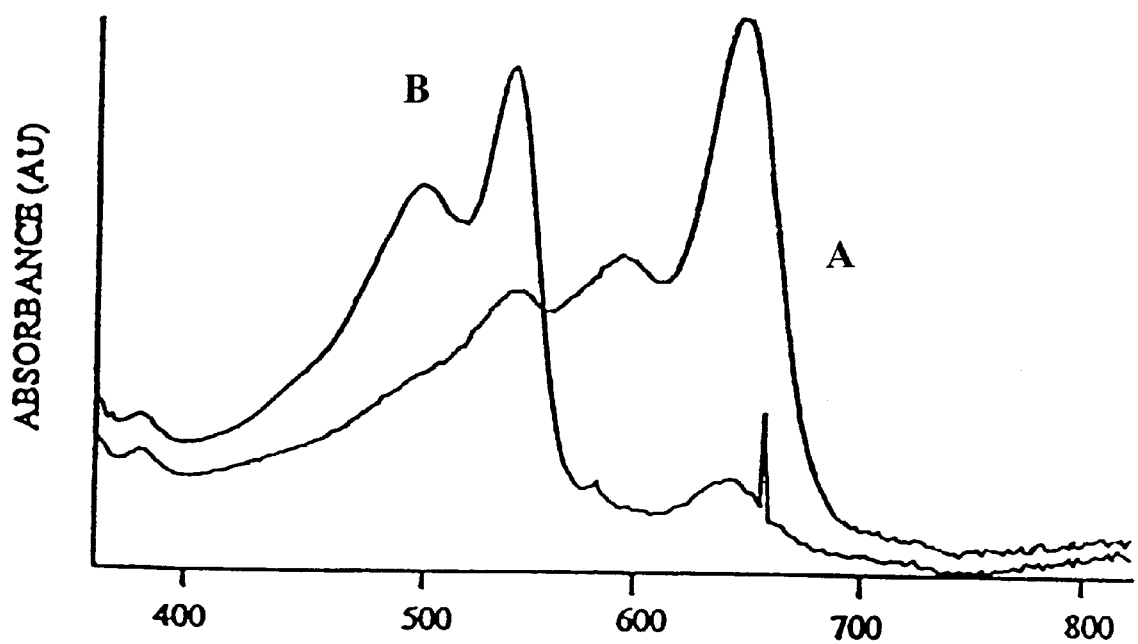
FIG. 8 shows a visible absorption spectrum of diacetylene material exposed to 1-octanol.
Figure 9A:
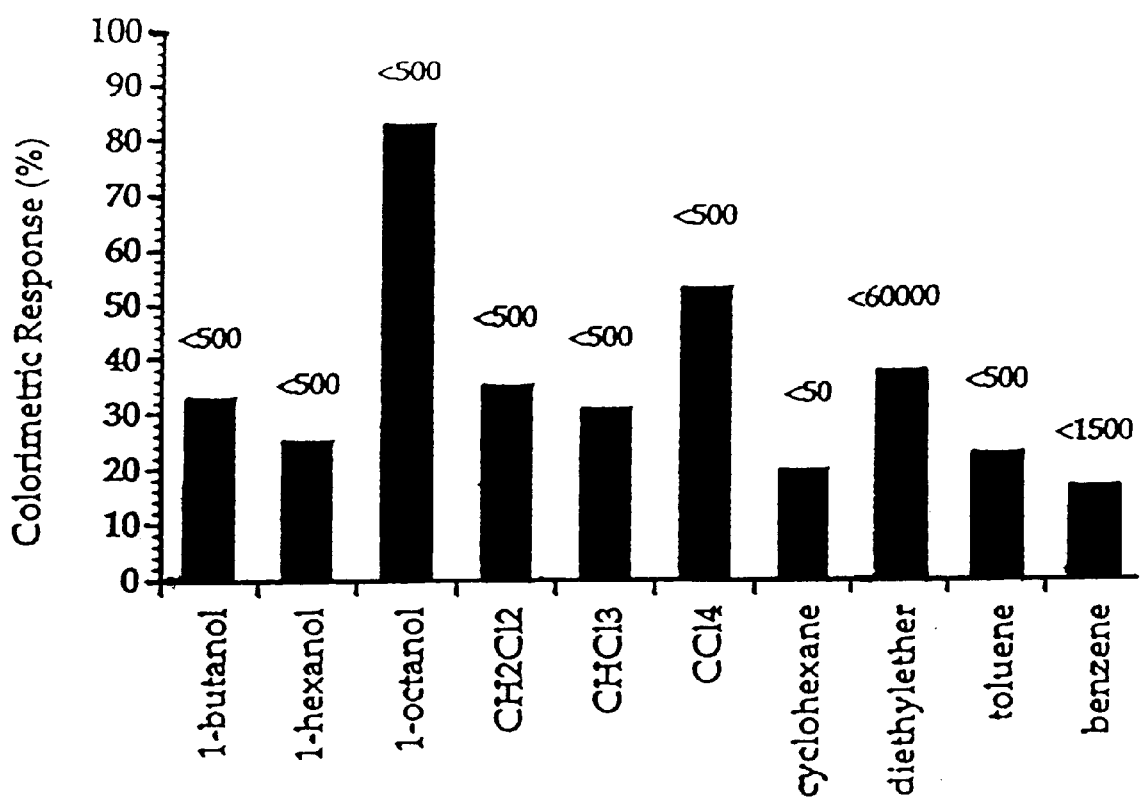
FIG. 9 shows a bar graph indicating colorimetric responses of PDA material to various VOCs and a table showing the concentration of the VOCs.

During the development of the present invention, it was observed that the interaction of volatile organic solvents with certain lipid-polymer membranes can produce a strong blue to red color transition. FIG. 8, curve a, shows the absorption spectrum of a p-PCA film in blue phase. The film changes to red phase p-PCA, curve b, upon exposure to approximately 500 ppm of 1-octanol dissolved in water. For a variety of solvents analyzed, the degree of color change was generally dependent upon the concentration of the solvent and also increased with the extent of halogenation and aromaticity. In this study, a single component thin membrane film of p-PCA was prepared and polymerized to the blue state by UV exposure (254 nm). These materials were more sensitive to water-immiscible solvents that to water-miscible solvents. For the miscible alcohols, it was found that the response increased dramatically for isopropanol compared to ethanol, perhaps because of a greater extent of solvent intercalation into the membrane. For the water-immiscible solvents, measurable color changes were obtained at 0.05 wt % (500 ppm). Within this group, a similar trend was observed with increased alcohol chain length, as well as with increased extent of chlorination. A wide variety of water-immiscible solvents were examined at their water-saturation concentration, as shown in FIG. 9. As indicated (FIG. 9B) each concentration is different. In FIG. 9A, the y-axis represents the colorimetric response, or the extent of blue-to-red conversion. The numbers above the bar represent an upper limit to the detection in ppm. For many of these solvents, it is clear that solvent concentrations well below 500 ppm can be detected.

Figure 10:
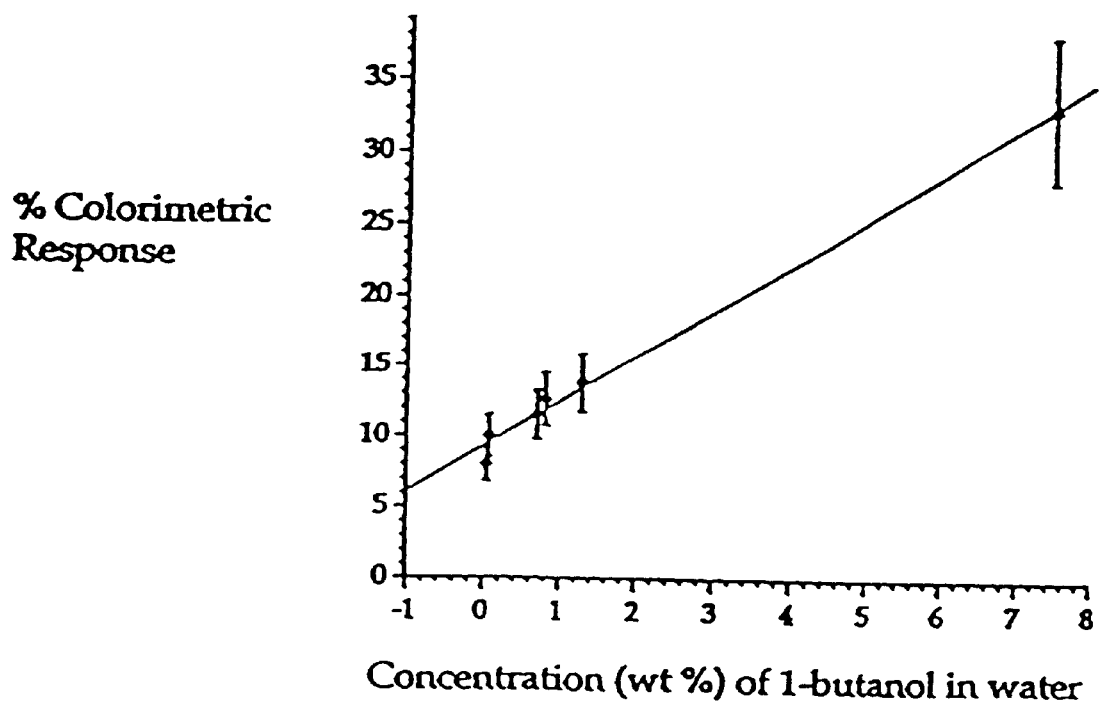
FIG. 10 shows a graph comparing calorimetric responses of 1-butanol to the concentration of 1-butanol.

For the immiscible solvents that have a relatively high solubility in water, it was possible to examine the effect of solvent concentration on the colorimetric response. A linear relationship was found to exist between the colorimetric response and solvent concentration in water in the range of 0.05–8 wt % as shown in FIG. 10 for 1-butanol.

In some embodiments, the presently claimed invention contemplates the generation of a large palette of polymerizable lipids of different headgroup chemistries to create an array. Lipids containing head groups with carboxylic acid functionalities (imparting a formal negative charge), hydrophilic uncharged hydroxy groups, primary amine functionalities (that may acquire a formal positive charge), amino derivatives (with positive, negative or zwitterionic charge), and hydrophobic groups can be generated. In some embodiments of the present invention, the combination of these materials into a single device facilitates the simultaneous detection of a variety of VOCs or the discrimination of a desired VOC from background interferants.

In other embodiments, the sol-gel glass material is customized, such that the pores serve as a size-selective screen to exclude potential interferants from the testing material. In addition, the sol-gel processes of the present invention allow structures to be formed that can be molded into any desirable shape. For example, in addition to their formulation into a convenient wearable cartridge, the coatings can also be prepared on cuvettes and microtiter plates for quick screening assays. Finally, the lipid-polymer membrane may be coated onto other optical measuring devices such as colorimeter or fiber optic tips, useful for cases where visual observation is inappropriate or does not provide the required level of sensitivity. The change in optical signal might then be coupled to an audio or vibratory "alarm" signal that provides a secondary level of warning. The sol-gel materials can also be processed to form monoliths, powders, and fibers. Such variability in material shape or form allow application of the biopolymeric material-based sensor materials of the present invention to most any platform, thereby improving portability, handling, durability, sensitivity, and storage time.

The pharmaceutical industry has an ongoing need for solvent sensors, as pharmaceutical compounds are typically manufactured through organic chemical reactions that take place in the presence of solvents. Before packaging of a drug for use in humans or other animals, the solvent must be completely driven off (Carey and Kowalski, Anal. Chem. 60: 541 [1988]). The currently used method for detecting these VOCs uses energy intensive dryers to blow hot air across the drug and piezoelectric crystal arrays to analyze the evaporation of the various solvents (Carey, Trends in Anal. Chem. 13; 210 [1993]). The presently claimed invention provides a colorimetric based approach that greatly simplify these measurements.

In addition, interest in analytical methods for the quantitation of VOCs in non-industrial indoor air environments has increased dramatically in the last 5 years. This is due primarily to a heightened awareness of emissions from common household appliances or office equipment, as well as trends in controlled building ventilation. Companies that produce consumer. products have an interest in serving this increased need by providing indoor air monitors that can deduce the presence of hazardous VOCs in-situ, without the need for air sampling and subsequent laboratory analysis. The presently claimed invention provides embodiments to achieve such means. Indeed, embodiments of the present invention provide for enhanced air sampling, and the cartridges may be connected to small, portable, battery-operated pumps for personal or general air sampling.

D. Other Examples

The examples provided above demonstrate the broad range of analytes detectable by the presently claimed invention, ranging from complex biological organisms (e.g., viruses, bacteria, and parasites) to simple, small organic molecules (e.g., alcohols). A number of other analytes have been successfully detected using ligands linked to biopolymeric material including, but not limited to botulinum neurotoxin detected with ganglioside incorporated p-PDA (Pan and Charych, Langmuir 13: 1367 [1997]). Thus, it is contemplated that numerous ligand types will be linked to self-assembling monomers using standard chemical synthesis techniques known in the art to detect a broad range of analytes. Additionally, numerous other ligand types can be incorporated into the biopolymeric matrix without covalent attachment to self-assembling monomer. These materials allow for the detection of small molecules, pathogens, bacteria, membrane receptors, membrane fragments, volatile organic compounds (VOCs), enzymes, drugs, and many other relevant materials.

The presently claimed invention also finds use as a sensor in a variety of other applications. The color transition of p-PDA materials is affected by changes in temperature and pH. Thus, the methods and compositions of the presently claimed invention find use as temperature and pH detectors.

Ligands can also be used in the present invention when they function as competitive binders to the analyte. For example, by measuring the colorimetric response to an analyte in the presence of a natural receptor for the analyte, one can determine the quantity and/or binding affinity of the natural receptor. Application of competition or inhibition techniques allow the testing of very small, largely unreactive compounds, as well as substances present in very low concentrations or substances that have a small number or single valiancy. One application of this technique finds use as a means for the development and improvement of drugs by providing a screening assay to observe competitive inhibition of natural binding events. The compositions of the presently claimed invention further provide means for testing libraries of materials, as the binding of desired material can be calorimetrically observed and the relevant biopolymeric material with its relevant ligand separated from the others by segregating out a particular polymeric structure (e.g., separating out a small portion of sol-gel material contained in an array).

EXPERIMENTAL

The following examples are provided in order to demonstrate and further illustrate certain preferred embodiments and aspects of the present invention and are not to be construed as limiting the scope thereof.

In the experimental disclosure which follows, the following abbreviations apply: N (normal); M (molar); mM (millimolar); $\mu$M (micromolar); mol (moles); mmol (millimoles); $\mu$mol (micromoles); nmol (nanomoles); pmol (picomoles); g (grams); mg (milligrams); $\mu$g (micrograms); ng (nanograms); 1 or L (liters); ml (milliliters); $\mu$l (microliters); cm (centimeters); mm (millimeters); $\mu$m (micrometers); nm (nanometers); $\mu$Ci (microcurie); mN (millinewton); N (newton); ° C.(degrees Centigrade); aq. (aqueous); J (Joule); PDA (diacetylene monomer); p-PDA (polymerized diacetylene); PCA (pentacosadiynoic acid monomer); p-PCA (polymerized pentacosadiynoic acid); OTS (octadecyltrichlorosilane); VOC (volatile organic chemical); CR (colorimetric response); pH (hydrogen ion concentration); AFM (atomic force microscopy); Hz (Hertz); LB (Langmuir-Blodgett); $CO_2$ (carbon dioxide); Sigma (Sigma Chemical Co., St. Louis, Mo.); Perkin-Elmer (Perkin-Elmer Co., Norwalk, Conn.); Fisher (Fisher Scientific, Pittsburgh, Pa.); and Farchan Laboratories (Farchan Laboratories, Inc., Gainesville, Fla.); Park Scientific Instrument (Park Scientific Instruments, Sunnyvale, Calif.); Biorad (Bio-Rad Laboratories, Hercules, Calif.); and Bellco Glass (Bellco Glass Inc., Vineland, N.J.).

All compounds were of reagent grade purity and used as supplied unless stated otherwise. Organic solvents were of spectral grade from Fisher Scientific. All aqueous solutions were prepared from water purified through a Barnstead Type D4700 NANOpure analytical Deionization System with Organic free cartridge registering an 18.0 M-Ohm-cm resistance.

EXAMPLE 1

Biopolymeric Material Preparation
Production of Liposomes

The self-assembling monomers to be incorporated into the liposomes were dissolved in solvent (e.g., chloroform for diacetylenes, methanol for ganglioside $G_{M1}$. Many other volatile solvents find use in the present invention, including, but not limited to, benzene, hexane, and ethylacetate. The solvent solutions were mixed in appropriate volumes to achieve the desired lipid mixture (e.g., 5% by mole of $G_{M1}$, 95% PCA) and a total lipid content of 2 $\mu$mol. The solvent was then evaporated by rotary evaporation or with a stream of nitrogen gas. The dried lipids were resuspended in sufficient de-ionized water to produce a 1–15 mM solution of lipid. The solution was then sonicated for 15–60 minutes with a probe sonicator (Fisher sonic dismembrator model 300, 50% output, microtip) as described by New (New, supra). The solution was heated during the sonication (in most cases the sonicating process alone provides sufficient heat) to a temperature above the phase transition of the lipids used (typically 30–90° C.). The resulting mixture was filtered through a 0.8 micromole nylon filter (Gelman) and cooled to 4° C. for storage or was polymerized.

In one embodiment, prior to polymerization, oxygen in the solution was removed by bubbling nitrogen through the sample for 5–10 minutes. Polymerization of the stirred liposome solution was conducted in a 1 cm quartz cuvette with a small 254 arn UV-lamp (pen-ray, energy: 1600 microwatt/cm$^2$) at a distance of 3 cm. The chamber was purged with nitrogen during the polymerization to replace all oxygen and to cool the sample. Polymerization times varied between 5 and 30 minutes depending on the desired properties (e.g., color, polymerization degree) of the liposomes.

In anther embodiment, the solution was placed in a UV-chamber, without purging, and exposed to 0.3–20 J/cm$^2$ of ultraviolet radiation, preferably 1.6 J/cm$^2$, for 5–30 minutes.

Production of Films

Polydiacetylene films were formed in a standard Langmuir-Blodgett trough (See e.g., Roberts, *Langmuir Blodgett Films*, Plenum, New York [1990]). The trough was filled with water to create a surface for the film. Distilled water was purified with a millipore water purifier with the resistivity of 18.2 M-Ohm. Diacetylene monomers (e.g., 5,7-docosadiynoic acid, 10,12-pentacosadiynoic acid [Farchan Laboratories], 5,7-pentacosadiynoic acid, combinations thereof, or other self assembling monomers), dissolved in a solvent spreading agent (e.g., spectral grade chloroform [Fisher]), were layered onto the aqueous surface with a syringe, to form a continuous film. Monomers prepared in the concentration range of 1.0 to 2.5 mM, were kept at a temperature of 4° C. in the dark, and were allowed to equilibrate at room temperature before being used in experiments.

Once layered on the water surface, the film was physically compressed using moveable barriers to form a tightly-packed monolayer of the self-assembling monomers. The monolayer was compressed to its tightest packed form (i.e., until a film surface pressure of 20–40 mN/m was achieved). Following compression, the film was polymerized.

Ultraviolet irradiation was used to polymerize the monomers, although other means of polymerization are available (e.g., gamma irradiation, x-ray irradiation, and electron beam exposure). Pressure was maintained on the film with the moveable barriers throughout the irradiation process at surface pressure of 20–40 mN/m. An ultraviolet lamp was placed 20 cm or farther from the film and trough. It was found that if the lamp is placed closer to the film damage to the diacetylene film may occur due to the effects of heating the film. The film was exposed to ultraviolet light with a wavelength of approximately 254 nm for approximately one minute. The polymerization was confirmed by observing the blue color acquired upon p-PCA formation and detecting the linear striations typical of p-PCA films with a polarizing optical microscope.

EXAMPLE 2

Sol-Gel Entrapment

A silica sol was prepared by sonicating 15.25 g of tetramethylorthosilicate (TMOS), 3.35 g of water, and 0.22 mL of 0.04 N aqueous hydrochloric acid in a chilled bath until the solution was one phase (approximately 20 minutes). Chilled MOPS buffer solution (50% v/v) was then added to the acidic sol making sure that the solution was well cooled in an ice bath to retard gelation. A variety of materials are appropriate for generating silica sols, including, but not limited to, any tetraalkoxysilane or organically modified silane (e.g., ormosil). Additionally, tetraethylorthosilicate (TEOS), methyltriethoxysilane (MeTEOS), aryl silsesquioxanes, and other metal oxides find use in generating sol-gel glass.

For encapsulating liposomes, a polymerized liposome solution (2.5 mL) (as generated in Example 1) was then mixed into the buffered sol (10 mL) and the mixture poured into plastic cuvettes, applied as a film on a flat surface, or poured into any other desired formation template, sealed with Parafilm, and allowed to gel at ambient temperature. Gelation of the samples occurred within a few minutes resulting in transparent, monolithic solids (18 mm×10 mm×5 mm) in the case of cuvette formed gels and as violet colored monoliths with p-PDA liposomes. Slight shrinkage of aged monoliths was observed due to syneresis.

The encapsulation of other biopolymeric material shapes (i.e., film and other nanostructures) can be conducted as described above. The materials must be generated or sectioned into small (i.e., nanoscopic) sized portions if not already so, and incorporated into a solution to be mixed with the buffered sol.

EXAMPLE 3

Attachment of Ligands

The self-assembling monomers can be synthesized to contain a large variety of chemical head-group functionalities using synthesis techniques common in the art. The ligands are then joined to the self-assembling monomers through chemical reaction with these functionalities using synthesis methods well known in the art. The functionalities include, but are not limited to, esters, ethers, amino, amides, or combinations thereof. Alternately, many ligands can be incorporated into the self-assembling matrix without covalent linkage to the surfactants (e.g., membrane proteins and molecules with hydrophobic regions such as gangliosides and lipoproteins).

Sialic acid was attached as ligand to diacetylene monomers. Several synthesis methods are well known in the art. In one embodiment, PDA (1.0 g, 2.7 mmol in chloroform) was reacted with N-hydroxy succinimide (NHS) (0.345 g, 3.0 mmol) and 1-(3-dimethylaminopropyl)-3-ethylcarbodiimide hydrochloride (EDC) (0.596 g, 3.1 mmol). The solution was stirred for 2 hours followed by evaporation of the chloroform. The residue was extracted with diethyl ether and water. The organic layer was dried with magnesium sulfate ($MgSO_4$) and filtered. The solvent was then evaporated by rotary evaporation to give 1.21 g of N-succinimidyl-PDA (NHS-PDA). Ethanolamine (0.200 mL, 2.9 mmol) was added to a solution of NHS-PDA (1.21 g in 50 mL of chloroform), followed by triethylamine (0.350 mL, 2.5 mmol) and stirred for two hours at room temperature. The solvent was evaporated and the residue purified by silica gel chromatography (2:1 EtOAc:hexane, $R_f$0.15) to give 0.99 g of N-(2-hydroxyethyl)-PDA.

Tetraethylene glycol diamine (1.26 g, 6.60 mmol) in 25 mL of chloroform was added to a solution of N-succinimidyl-PDA (0.603 g, 1.28 mmol) in 20 mL of chloroform, dropwise, with stirring, over a period of 30 minutes. The reaction was stirred for an additional 30 minutes before removal of the solvent by rotary evaporation. The residue was dissolved in EtoAc and extracted twice with water. The organic layer was dried with $MgSO_4$, and the solvent removed by rotary evaporation. The extract was purified by silica gel chromatography (20:1 $CHCl_3$:MeOH, $R_f$0.20) to give 3.72 g of N-(11-amino-3,6,9-trioxyundecanyl)-PDA.

Two mL of acetic anhydride was added to a cooled solution of ethyl-5-N-acetyl-2,6-anhydro-3,5-dideoxy-2-C-(2-propenyl)-D-erythro-L-mannonononate (0.47 g, 1.30 mmol) in 1.7 mL of pyridine under nitrogen, with stirring. The reaction was allowed to warm to room temperature overnight. After 18 hours, the solvents were removed under reduced pressure at ambient temperature, to yield a crude viscous oil. The oil was solidified by repeated evaporation from toluene. The crude solid was flash chromatographed over silica with ethylacetate as eluent, producing 0.58 g of ethyl-5-N-acetyl-4,7,8,9-tetra-O-acetyl-3,5-dideoxy-2-C-(2-propenyl)-D-erythro-L-manno-nononate.

A solution of ethyl-5-N-acetyl-4,7,8,9-tetra-O-acetyl-3,5-dideoxy-2-C-(2-propenyl)-D-erythro-L-manno-nononate (0.38 g, 0.72 mmol) in 10 mL of acetone was cooled to $-78°$ C. while protected from moisture with a $CaCl_2$ drying tube. Ozone was aspirated into the solution until the characteristic blue color persisted for 5 minutes. The reaction was purged with $O_2$ to dissipate the excess $O_3$, followed by warming to 5 ° C. Excess Jones' reagent (7 drops) was added until a rust orange color persisted, then the reaction was warmed to ambient temperature. After several minutes, ethanol was added dropwise to consume the excess oxidant. The green precipitate was filtered and washed with acetone several times. The combined filtrates were evaporated in vacuuo and dissolved in ethylacetate. The solution was extracted with saturated aq. $NaHCO_3$ solution three times. The combined aqueous layers were acidified with concentrated HCl and extracted 5 times with methylene chloride. The combined methylene chloride extracts were dried with $MgSO_4$, filtered and evaporated in vacuuo to give ethyl-5-N-acetyl-4,7,8,9-tetra-O-acetyl-3,5-dideoxy-2-C-(acetic acid)-D-erythro-L-manno-nonate.

Ethyl-5-N-acetyl-4,7,8,9-tetra-O-acetyl-3,5-dideoxy-2-C-(acetic acid)-D-erythro-L-manno-nonate (0.194 g, 0.35 mmol) was added to a cooled solution (5° C.) NHS (0.058 g, 0.50 mmol) and EDC (0.096 g, 0.50 mmol) in 2 mL of chloroform, under nitrogen. The reaction was warmed to ambient temperature with stirring for 5 hours. The reaction was then diluted with 15 mL of chloroform and washed with 1N HCl (aq.), twice; saturated (aq.) sodium bicarbonate, twice; and saturated (aq.) sodium chloride, once. The organic layer was dried over $MgSO_4$, filtered, and evaporated to form ethyl-5-N-acetyl-4,7,8,9-tetra-O-acetyl-3,5-dideoxy-2-C-(N-succinimidylacetate)D-erythro-L-manno-nononate Ethyl-5-N-acetyl-4,7,8,9-tetra-O-acetyl-3,5-dideoxy-2-C-(N-succinimidylacetate)-D-erythro-L-manno-nononate (0.143 g, 0.22 mmol) and N-(11-amino-3,6,9-trioxyundecanyl)-PDA (0.133 g, 0.24 mmol) were dissolved in 2 mL of chloroform and the reaction was sealed and stirred for 56 hours, The solution was diluted with 15 mL of chloroform and washed with sodium chloride saturated 1N HCl (ag.), twice; saturated (ag.) sodium bicarbonate, twice; and saturated (ag.) sodium chloride, once. The organic layer was dried over $MgSO_4$, filtered, and evaporated to a crude semi-solid. The material was flash chromatographed over silica (20:1 $CHCl_3$:MeOH), producing ethyl-5-N-acetyl-4, 5,8,9-tetra-O-acetyl-3,5-dideoxy-2-C-[(N-11'-(PDA)-3',6', 9'-trioxyundecanyl)acedamido]-D-erythro-L-manino-nononate The sialic acid derived-PDA was formed by dissolving ethyl-5-N-acetyl-4,5,8,9-tetra-O-acetyl-3,5-dideoxy-2-C-[(N-11'-(PDA)-3',6',9'-trioxyundecanyl)acedamido]-D-erythro-L-manno-nononate (0.20 g, 0.19 mmol) in a solution of 4 mL of water and 0.5 mL of methanol containing 0.1 g dissolved sodium hydroxide. The solution was stirred for 3 hours, and ion exchange resin (Biorad AG 50W-X4 H+form) was added until the solution was acidic to pH paper. The solution was filtered and the filtrate evaporated in vacuo, producing sialic acid derived-PDA.

In other embodiments, carbohydrates (including sialic acid) can be modified by a three-step procedure to produce N-allyl glycosides. The N-allyl glycosides can then be easily linked to other molecules (e.g., PDA) using simple chemical synthesis means routine in the art. This method provides a means to incorporate a broad range of carbohydrates into biopolymeric material (and thus provides a means to detect a broad range of analytes). First, oligosaccharides are dissolved in neat allyl amine (water may be added if necessary and does not adversely affect the yield) producing a 0.5–0.1 M solution. The reaction is stopped and stirred for at least 48 hours (small aliquots can be removed and assay for reaction completeness as described below). Upon complete conversion of the starting material into amino glycoside product, the solvent is removed by evaporation and the crude solid is treated with toluene and evaporated to dryness several times. The solid is then chilled in an ice bath and a solution of 60% pyridine, 40% acetic anhydride is added to give a solution containing five hundred mole percent excess of acetic anhydride. The reaction is protect from moisture, stirred and allowed to warm to ambient temperature overnight. The solvents are removed by evaporation and the residue is dissolved in toluene and dried by evaporation several times. The crude product is purified by flash chromatography producing the peracetylated NAc-allyl glycoside form of the free sugars.

The peracetylated NAc-allyl glycosides are then dissolved in anhydrous methanol to give a 0.1–0.01 M solution. Several drops of 1 N NaOMe in MeOH are added and the reaction stirred at ambient temperature for 3 hours. Enough Dowex 50 resin (H+form) is added to neutralize the base, then the solution is filtered and evaporated to dryness (purification by recrystallization can be conducted if desired). The products are the N-allyl glycoslamide form of the carbohydrates. These synthesis reactions have produced the N-allyl glycoslamide forms of a variety of carbohydrates, including, but not limited to, glucose, NAc-glucosamine, fucose, lactose, tri-NAc-Chitotriose, Sulfo Lewis$^x$ analog and Sialyl Lewis$^x$ analog.

Ganglioside $G_{M1}$ presents an example of incorporation of a ligand without covalent attachment to the self-assembling monomers. Ganglioside $G_{M1}$ was introduced in the biopolymeric material by combining a solution of methanol dissolved ganglioside $G_{M1}$ (Sigma) with chloroform dissolved p-PDA, and dried. The ganglioside contains a hydrophobic region that facilitates its incorporation into self-assembling surfactant structures. Thus, when the dried solutions were resuspended in deionized water, the resulting structures contained a mixture of ganglioside and p-PDA.

The generation of PDA-linked ligands containing a variety of different chemical head-group species is described in Example 5, for VOC detection. These examples demonstrate the derivation of PDA with a broad range of chemical head groups such as hydrophilic uncharged hydroxyl groups, primary amine functionalities, amino acid derivatives, and hydrophobic groups. These and other modifications are generated by synthesis methods common in the art.

The NHS-PDA, as generated above, and thiol-linked PDA provide functional groups for the attachment of proteins and antibodies. The NHS or thiol-linked monomers are incorporated into the desired aggregate and polymerized. The NHS or thiol functional groups then provide a surface reaction site for covalent linkage to proteins and antibodies using chemical synthesis reactions standard in the art. In another embodiment, a hydrazide functional group can be place on PDA, allowing linkage to aldehydes and ketone groups of proteins and antibodies. These embodiments provide a means to incorporate an extremely broad array of proteins and antibodies onto the biopolymeric material.

In other embodiments, various other surfactant-linked ligands can be prepared using condensation reactions involving an activated carboxylic acid group and a nucleophilic amino or hydroxy. PDA can be activated with trimethylacetylchloride under anhydrous conditions to form an active asymmetric anhydride. The anhydride can be treated with excess ethylene diamine or ethanolamine to form ethylenediamino-PDA (EDA-PDA) or ethanolamine-PDA (EA-PDA), respectively. One and a half mole equivalents of triethylamine are added as a catalytic base and reactions are allowed to proceed for three hours at room temperature: EDA-PDA and EA-PDA are chromatographically purified using a silica gel column and a chloroform/methanol gradient. The EDA-PDA or EA-PDA are then be condensed with free carboxylic acid containing ligands (chemically activated as above) to form the ligand-linked polymerizable surfactants. Representative examples of ligands that can be prepared by this method include, but are not limited to, carbohydrates, nucleotides, and biotin.

The art contains numerous other examples of successful linkage or association of ligands. The self-assembling monomers can be of modified chain length or may consist of double or multiple chains. These various combinations of ligands and monomers provide an extremely broad array of biopolymeric materials appropriate for the detection of a broad range of analytes, with the desired colorimetric response, selectivity, and sensitivity.

EXAMPLE 4

Characterization Methods

I. Visible Absorption Spectroscopy

Visible absorption studies were performed using a Hewlett Packard 8452A Diode array spectrophotometer. For p-PDA material (i.e., films, liposomes, and sol-gel entrapped materials), the calorimetric response (CR) was quantified by measuring the percent change in the absorption at 626 nm (which imparts the blue color to the material) relative to the total absorption maxima.

In order to quantify the response of a biopolymeric material to a given amount of analyte, the visible absorption spectrum of the biopolymeric material without the analyte was analyzed as $$B_o = I_{626}/(I_{536} + I_{626})$$

where $B_o$ is defined as the intensity of absorption at 626 nm divided by the sum of the absorption intensities at 536 and 626 nm. The biopolymeric material exposed to analytes were analyzed in the same manner as $$B_a = I_{626}/(I_{536} + I_{626})$$

where $B_a$ represents the new ratio of absorbance intensities after incubation with the analyte. The calorimetric response (CR) of a liposome solution is defined as the percentage change in B upon exposure to analyte.

$$CR = [(B_o - B_a)/B_o] \times 100\%$$

Figure 6:
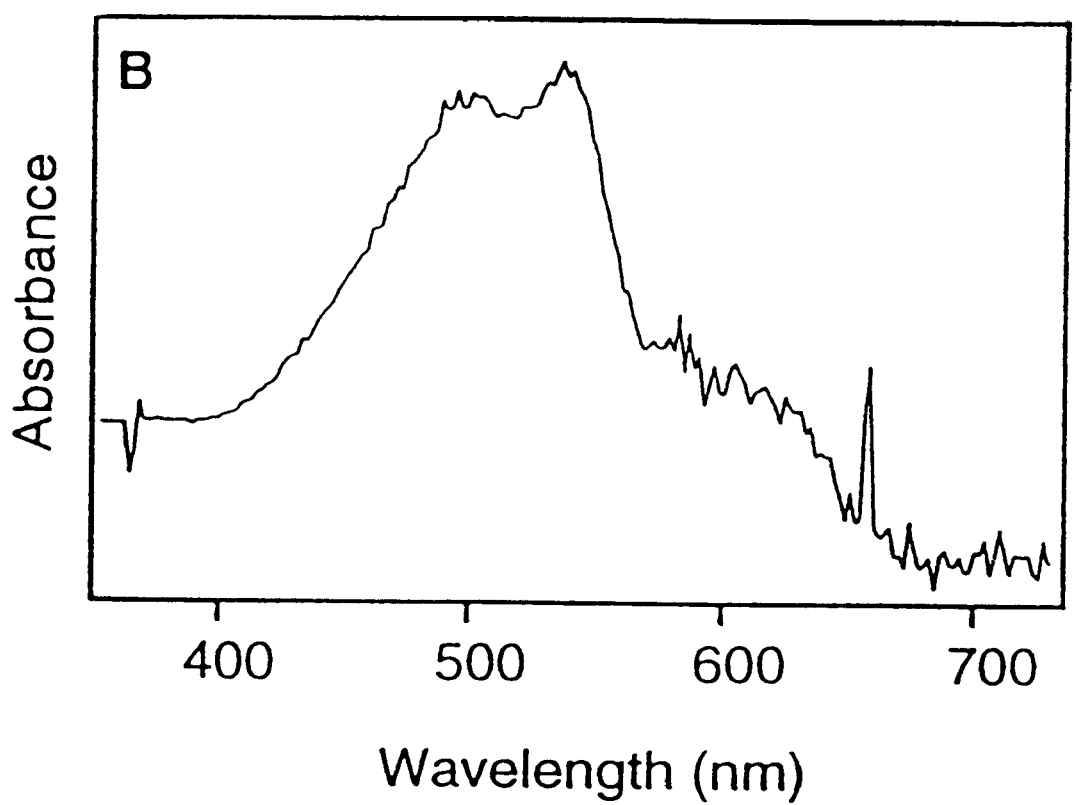
FIG. 6 shows a visible absorption spectrum of "red phase," sialic acid-linked DCDA liposomes entrapped in sol-gel glass.
Figure 7:
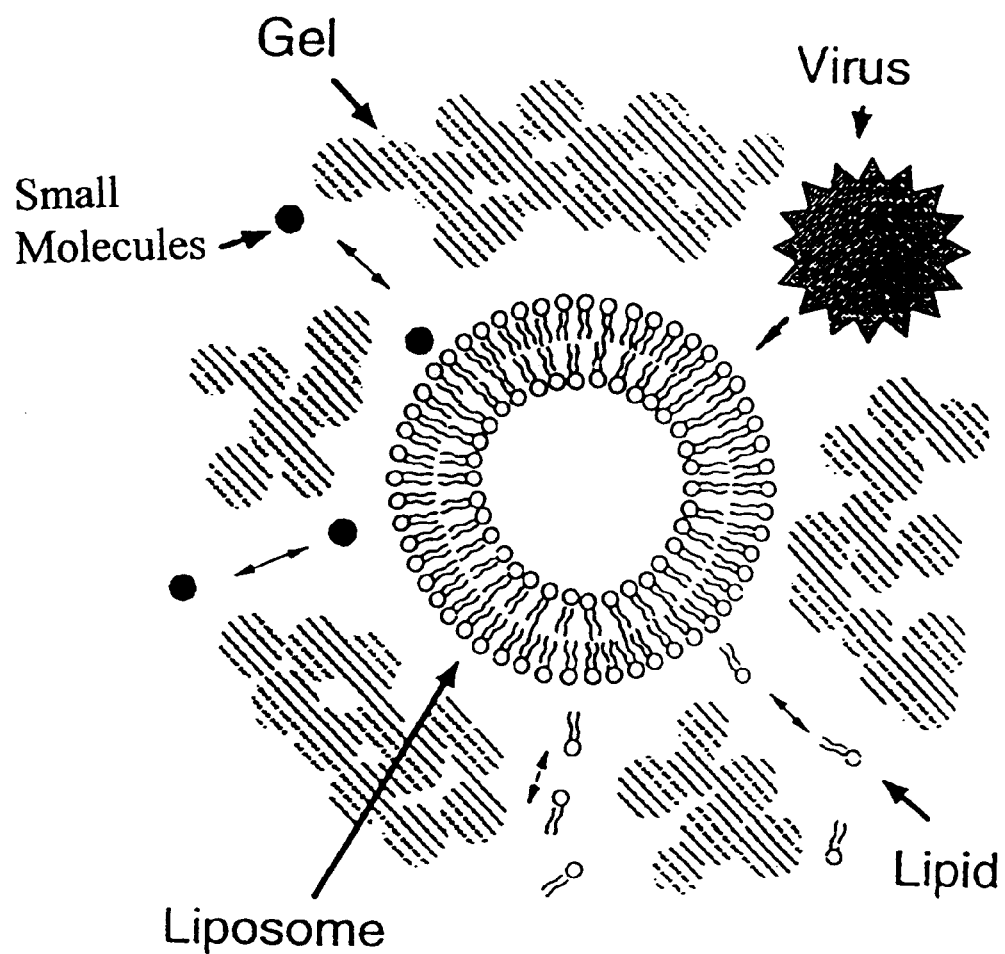
FIG. 7 shows a representation of the porous structure of sol-gel-prepared material acting as a size selective barrier.
Figure 11A:
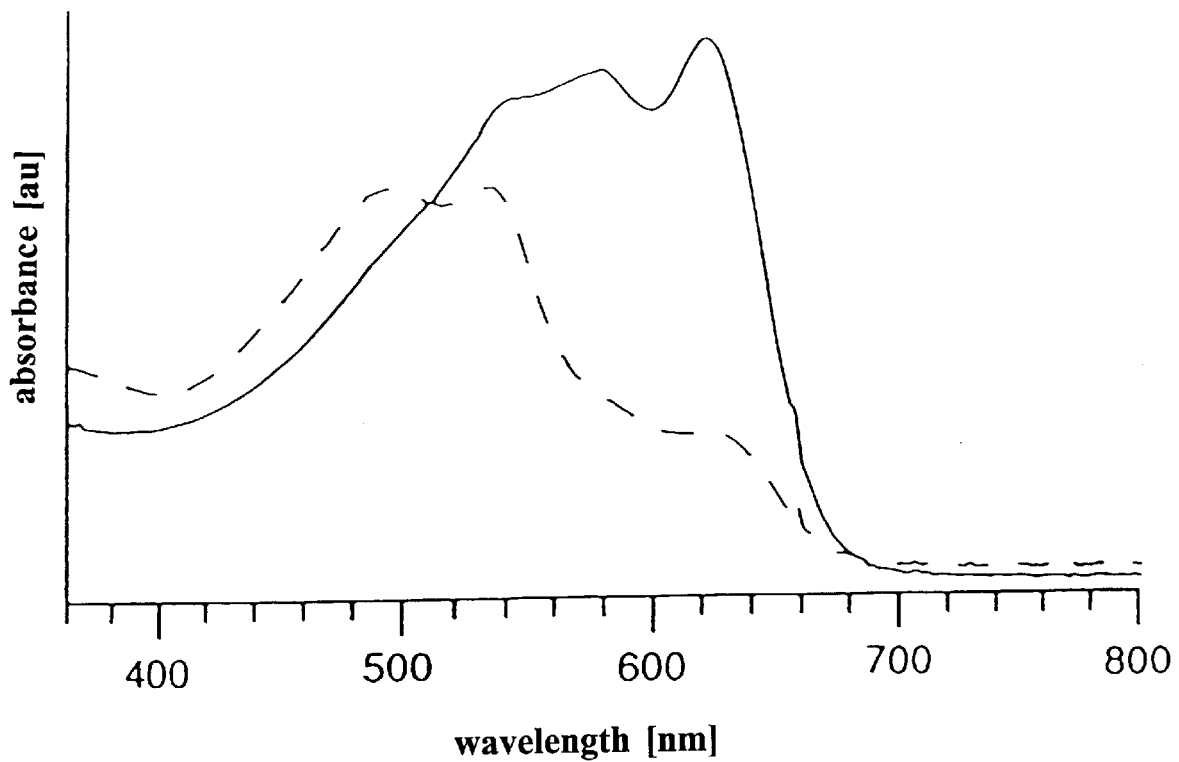
FIG. 11 shows a visible absorption spectrum of sialic acid-linked PDA before (solid line) and after (dashed line) exposure to influenza virus for: A) blue/pink form; and B) purple/orange form material.
Figure 11B:
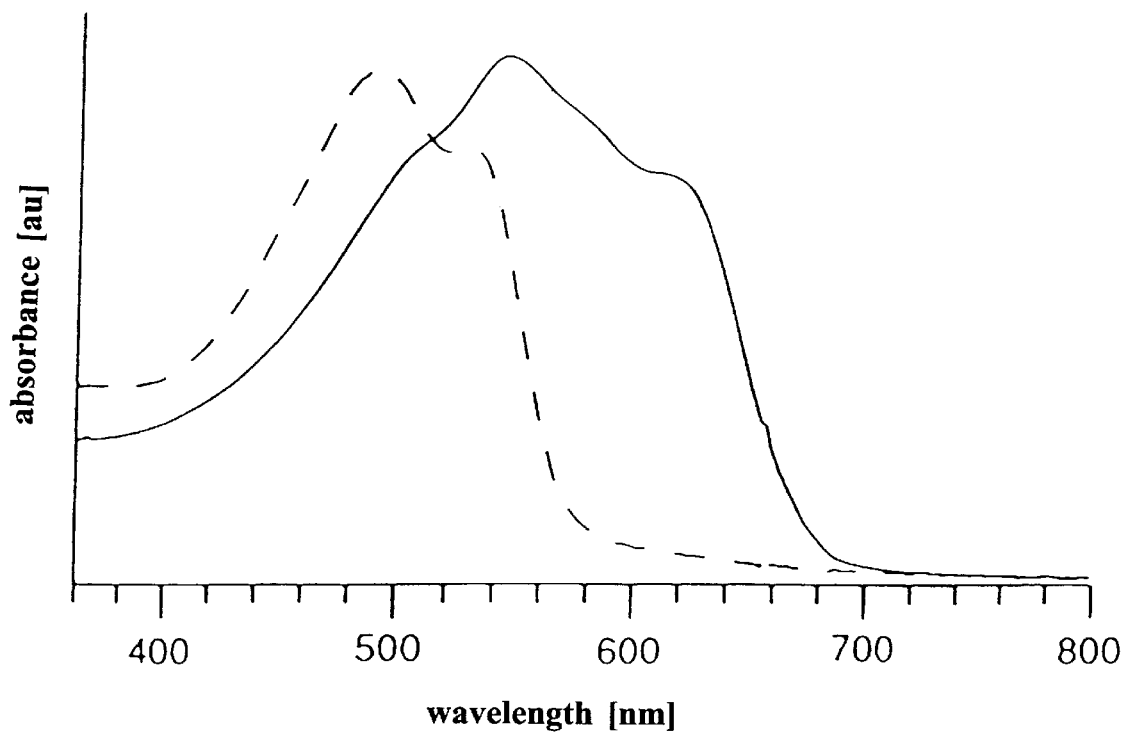
Figure 13:
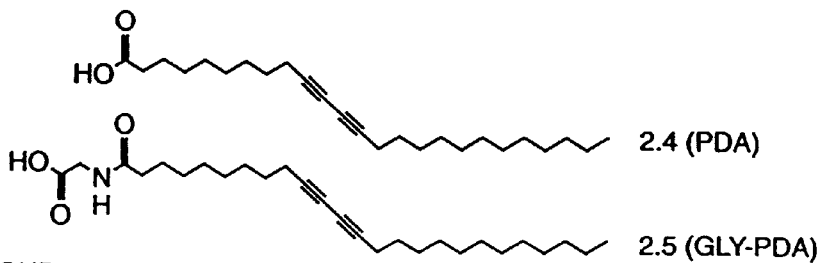
FIG. 13 shows derivations of PDA for use in detection arrays.
Figure 13:
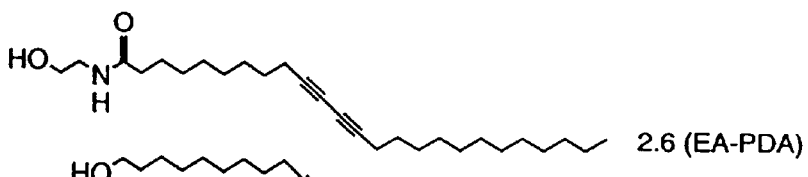
Figure 13:
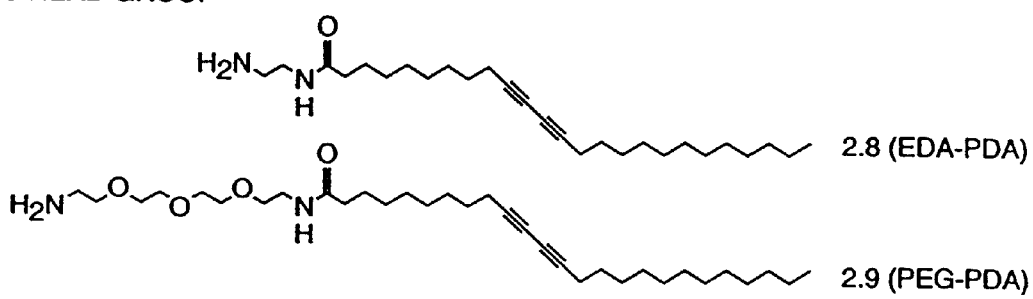
Figure 13:
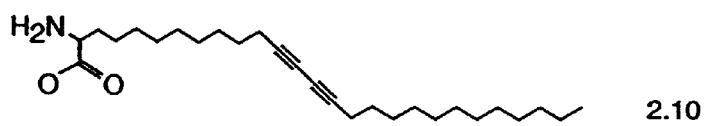
Figure 13:
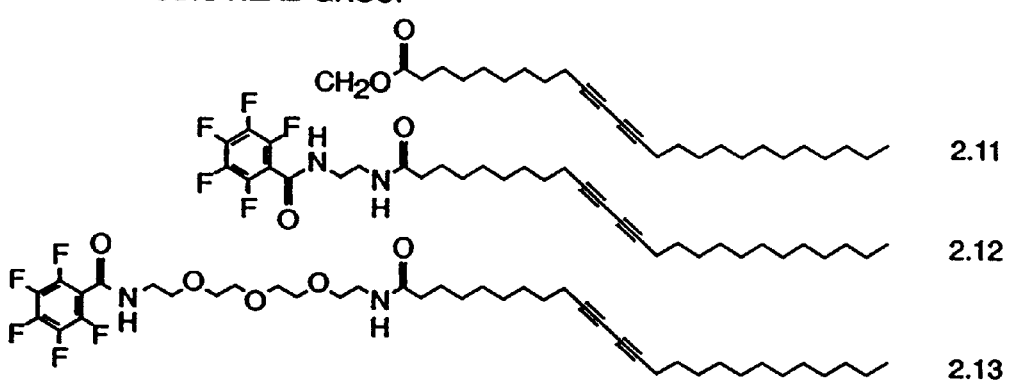
Figure 14:
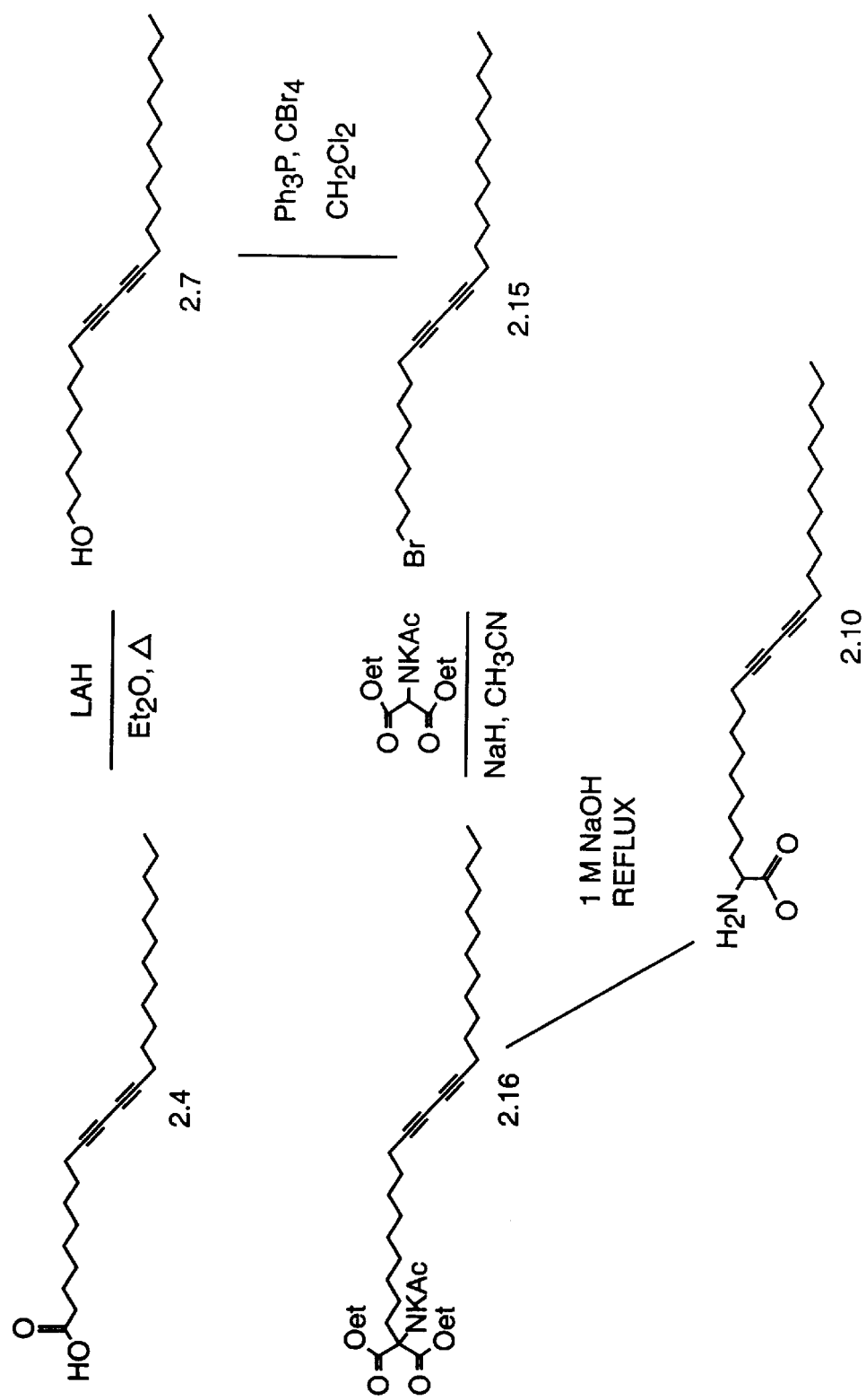
FIG. 14 shows the organic synthesis of compound 2.10.

Data demonstrating such determinations are presented in various Figures, including FIG. 9 (showing calorimetric responses from VOCs), FIG. 11 (showing calorimetric response to influenza virus with A) blue liposome solution before (solid line) and after (dashed line) viral exposure and B) purple liposome solution before (solid line) and after (dashed line) viral exposure), FIG. 12 (showing calorimetric response from cholera toxin A) before and B) after exposure), and FIG. 6 (showing absorbances from influenza virus interactions with sol-gel entrapped p-PDA). In FIG. 6, a p-PDA liposome/sol-gel monolith was incubated in 50 mM Tris buffer at pH 7.0 in a plastic cuvette. A 50 μl aliquot of influenza A X31 was added to the cuvette and the visible absorption spectra were recorded as a function of time from 360 to 800 nm.

Atomic Force Microscopy

In situ atomic force microscopy was used to reveal the morphology, surface topography, and growth and dissolution characteristics of microscopic biopolymeric crystals, and allowed dynamic observations of nucleation events and the determination. Studies were conducted using standard techniques for in situ studies as described by Binnig et al. (Binnig et al., Phys. Rev. Lett. 12: 930 [1986]; and Binnig et al., Europhys. Lett. 3: 1281 [1987])

Two different atomic force microscopes were used in this study. Images larger than 1 $\mu m^2$ were acquired with a commercially available instrument (Park Scientific Instrument). In this case Si ultralevers (Park Scientific Instrument) were used. Commercially available photolithographically patterned glass slides (Bellco Glass) were used to allow imaging of the exact same region of the film after each temperature step. Images smaller than 1 $\mu m^2$ were taken with a home-built AFM (Kolbe et al., Ultramicroscopy 42–44: 1113 [1992]). $Si_3N_4$ cantilevers with a nominal force constant of 0.1 N/m were used (Park Scientific Instruments). Both microscopes were operated in contact mode, and in the latter case a four-quadrant position-sensitive photodiode allowed the measurement of the cantilever bending and twisting simultaneously. All images were acquired in contact mode under ambient conditions.

EXAMPLE 5

Detection of Analytes

Detection of Influenza Virus

Sialic acid linked biopolymeric material was generated as described in Examples 1–3. The materials, either in sol-gel or alone, were exposed to influenza virus and colorimetric information was observed visually or with spectroscopy as described in Example 4, and shown in FIGS. 5 and 6 for blue and red phase material, respectively. For liposomes, a 1–10% mixture of sialic acid-linked PCA was incorporated, as previous studies indicated that optimum viral binding occurs for mixtures of 1–10% in liposomes (Spevak et al., J. Am. Chem. Soc. 161: 1146 [1993]).

For silicate glass-entrapped liposomes, it was found that 5,7-DCDA provided a more vivid colorimetric response than 10,12-p-PCA. It is believed that the improved response with 5,7-DCDA was related to the size restrictiveness of the sol-gel material and the topochemical nature of the conformational changes responsible for the chromatic transitions, although an understanding of the mechanism is not required to practice the present invention.

In one experiment, irradiation of a sialic acid-linked p-PCA containing liposome solutions for 5–10 minutes resulted in the formation of deeply blue colored liposomes, while polymerization for between 10 and 30 minute resulted in a purple color. When influenza virus was added to the liposomes, the material changed to a pink or orange color, depending on whether the initial preparation was blue or purple, respectively. These color changes were readily visible with the naked eye.

Competitive inhibition experiments were conducted to demonstrate the specificity of the ligand-analyte interaction. Experiments were performed as described above, but with a slight excess of a-O-methyl-neuramatic acid, a known inhibitor for influenza virus hemagglutination. The presence of the inhibitor resulted in no detectable color change of the biopolymeric material.

Detection of VOCs

Biopolymeric material was generated as described in Examples 1 and 3, and can be incorporated into porous sol-gel material using the sol-gel method as describe in Example 2. The sol-gel/biopolymeric material is then molded into a desired shape and used directly for VOC detection.

VOCs were introduced to p-PDA film in the blue phase and chromatic transitions from blue phase to red phase were measured by detecting visible absorption spectra as described in Example 4. Colorimetric response was measured for 1-butanol, 1-hexanol, 1-octanol, $CH_2Cl_2$, $CHCl_3$, $CCl_4$, cyclohexane, diethylether, toluene, and benzene with the data presented in FIG. 9 (as described earlier). The number values above each bar represent the range in parts per million, that produced the indicated colorimetric responses.

A large palette of polymerizable lipids of different head-group chemistries can be generated to create an array. FIG. 13 depicts the lipids for incorporation into sol-gel matrix. These may be categorized into five groups based upon their head group functionality. Compounds 2.4 and 2.5 contain carboxylic acid functionalities, imparting a formal negative charge. Compounds 2.6 and 2.7 contain a hydrophilic uncharged hydroxyl group. Compounds 2.8 and 2.9 have primary amine functionalities that may acquire a formal positive charge. The amino acid derivative 2.10 may exist with positive, negative or zwitterionic charge. Compounds 2.11–2.13 have hydrophobic head groups.

The synthesis of these lipids begins with commercially available PDA (2.4). Synthesis of all but 2.10, 2.12, and 2.13 can be carried out by coupling the respective head group to PDA utilizing the activated N-hyroxysuccinimidyl ester of PDA (NHS-PDA) as described in Example 3. The amino acid lipid 2.10 can be prepared in four steps from PDA as shown in FIG. 14, using lithium aluminum hydride and transformation of the alcohol to the corresponding bromide derivative. The bromide is converted to the protected amino acid by reaction with diethyl N-acetimidomalonate in acetonitrile with sodium hydride, followed by deprotection. The fluorinated lipids 2.12 and 2.13 can be prepared by the reaction of pentafluorobenzoyl chloride with amino lipids 2.8 and 2.9.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A method for detecting analytes, comprising:

a) providing:

i) colorimetric diacetylene polymers encapsulated in porous sol-gel glass;

ii) a detector; and iii) a sample suspected of comprising one or more analytes;

b) exposing said colorimetric diacetylene polymers encapsulated in porous sol-gel glass to said sample such that said one or more analytes in said sample reacts with said colorimetric diacetylene polymers causing a conformational change in said colorimetric diacetylene polymers, wherein said conformational change produces a colorimetric response;

c) observing said colorimetric response using said detector; and d) correlating said response to the presence or absence of said one or more analytes id said sample.

2. The method of claim 1, wherein said sol-gel glass comprises tetramethylorthosilicate.

3. The method of claim 1, wherein said colorimetric diacetylene polymers encapsulated in porous sol-gel glass are selected from the group consisting of liposomes, films, multilayers, braided, lamellar, helical, tubular, and fiber-like shapes, solvated rods, solvated coils, and combinations thereof.

4. The method of claim 1, wherein said colorimetic diacetylene polymers encapsulated in porous sol-gel glass are selected from the group consisting of 5,7-docosadiynoic acid, 10,12-pentacosadiynoic acid, 5,7-pentacosadiynoic acid, and combinations thereof.

5. The method of claim 1, wherein said colorimetric diacetylene polymers encapsulated in porous sol-gel glass contain head groups selected from the group consisting of carboxylic acid, hydroxyl groups, amine groups, amino acid derivatives, and hydrophobic groups.

6. The method of claim 1, wherein said colorimetric diacetylene polymers encapsulated in porous sol-gel glass comprises a ligand.

7. The method of claim 6, wherein said ligand is selected from the group consisting of peptides, carbohydrates, nucleic acids, biotin, drugs, chromophores, antigens, chelating compounds, molecular recognition complexes, ionic groups, polymerizable groups, linker groups, electron donors, electron acceptor groups, hydrophobic groups, hydrophilic groups, receptor binding groups, antibodies, and combinations thereof.

8. The method of claim 1, wherein said analyte is selected from the group consisting of small molecules, pathogens, bacteria, membrane receptors, membrane fragments, enzymes, drugs, antibodies, and combinations thereof.

9. The method of claim 1, wherein said detection means is selected from the group consisting of visual inspection, spectrometry, optical fiber, quartz oscillators, electrode surfaces, and scintillation.

10. The method of claim 1, wherein said calorimetric response is used as a competitive binding measurement to quantitate and characterize the presence of natural binding sites.

11. The method of claim 1, wherein said calorimetric diacetylene polymers encapsulated in porous sol-gel glass comprises an array.

12. A method for detecting analytes, comprising:
 a) providing:
    i) colorimetric diacetylene polymers encapsulated in porous sol-gel glass; and
    ii) a sample suspected of comprising one or more analytes;
 b) exposing said colorimetric diacetylene polymers encapsulated in porous sol-gel glass to said sample under conditions such that said one or more analytes in said sample reacts with said colorimetric diacetylene polymers causing a conformational change in said colorimetric diacetylene polymers, wherein said conformational change produces a colorimetric response; and
 c) observing said colorimetric response.

13. The method of claim 12, wherein said porous sol-gel glass comprises tetramethylorthosilicate.

14. The method of claim 12, wherein said colorimetric diacetylene polymers encapsulated in porous sol-gel glass assemble to form nanostructures selected from the group consisting of liposomes, films, multilayers, braided, lamellar, helical tubular, and fiber-like shapes, solvated rods, solvated coils, and combinations thereof.

15. The method of claim 12, wherein said colorimetric diacetylene polymers encapsulated in porous sol-gel glass are selected from the group consisting of 5,7-docosadiynoic acid, 10,12-pentacosadiynoic acid, 5,7-pentacosadiynoic acid, and combinations thereof.

16. The method of claim 12, wherein said colorimetric diacetylene polymers encapsulated in porous sol-gel glass contain head groups selected from the group consisting of carboxylic acid, hydroxyl groups, amine groups, amino acid derivatives, and hydrophobic groups.

17. The method of claim 12, wherein said colorimetic diacetylene polymers encapsulated in porous sol-gel glass comprises a ligand.

18. The method of claim 17, wherein said ligand is selected from the group consisting of peptides, carbohydrates, nucleic acids, biotin, drugs, chromophores, antigens, chelating compounds, molecular recognition complexes, ionic groups, polymerizable groups, linker groups, electros donors, electron acceptor groups, hydrophobic groups, hydrophilic groups, receptor binding groups, antibodies, and combinations thereof.

19. The method of claim 12, wherein said analyte is selected from the group consisting of small molecules, pathogens, bacteria, membrane receptors, membrane fragments, enzymes, drugs, antibodies, and combinations thereof.

20. The method of claim 12, wherein said colorimetric diacetylene polymers encapsulated in porous sol-gel glass comprises a badge.

21. The method of claim 12, wherein said observing is conducted using a means selected from the group consisting of visual inspection, spectrometry, optical fiber, quartz oscillators, electrode surfaces, and scintillation.

22. The method claim 12, wherein said colorimetic response is used as a competitive binding measurement to quantitate and characterize the presence of natural binding sites.

23. The method of claim 12, wherein said colorimetric diacetylene polymers encapsulated in porous sol-gel glass comprises an array.

* * * * *

UNITED STATES PATENT AND TRADEMARK OFFICE
CERTIFICATE OF CORRECTION

PATENT NO. : 6,485,987 B1
DATED : November 26, 2002
INVENTOR(S) : Charych et al.

It is certified that error appears in the above-identified patent and that said Letters Patent is hereby corrected as shown below:

<u>Column 1,</u>
Line 4, please insert the following paragraph:

-- This invention was made during work partially supported by the U.S. Department of Energy under Contract No.: DE-AC03-76SF00098. The government may have certain rights in the invention. --

Signed and Sealed this

Fourth Day of March, 2003

JAMES E. ROGAN
*Director of the United States Patent and Trademark Office*